(12) United States Patent
Abraham et al.

(10) Patent No.: US 12,115,210 B2
(45) Date of Patent: Oct. 15, 2024

(54) LONG ACTING AMYLIN RECEPTOR AGONISTS AND USES THEREOF

(71) Applicant: Eli Lilly and Company, Indianapolis, IN (US)

(72) Inventors: Milata Mary Abraham, Indianapolis, IN (US); Daniel Anthony Briere, Morgantown, IN (US); Lili Guo, Carmel, IN (US); Samantha Grace Lyons Keyser, Carmel, IN (US); John Lee, Torrance, CA (US); Hongchang Qu, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/684,578

(22) Filed: Mar. 2, 2022

(65) Prior Publication Data

US 2022/0288168 A1    Sep. 15, 2022

Related U.S. Application Data

(60) Provisional application No. 63/155,894, filed on Mar. 3, 2021.

(51) Int. Cl.
  *A61K 38/22*   (2006.01)
  *A61P 3/04*    (2006.01)
  *C07K 14/575*  (2006.01)

(52) U.S. Cl.
  CPC .......... *A61K 38/2235* (2013.01); *A61K 38/22* (2013.01); *A61P 3/04* (2018.01); *C07K 14/575* (2013.01)

(58) Field of Classification Search
  None
  See application file for complete search history.

(56) References Cited

U.S. PATENT DOCUMENTS

| | | | |
|---|---|---|---|
| 8,575,090 B2 | 11/2013 | Schaeffer et al. | |
| 8,722,849 B2 | 5/2014 | Schaeffer et al. | |
| 8,741,836 B2 | 6/2014 | Schaeffer et al. | |
| 9,023,789 B2 | 5/2015 | Dahl et al. | |
| 9,029,325 B2 | 5/2015 | Schaeffer et al. | |
| 10,071,140 B2 | 9/2018 | Mathiesen et al. | |
| 2009/0286723 A1* | 11/2009 | Levy | A61P 9/00 530/308 |
| 2014/0087995 A1 | 3/2014 | Dahl et al. | |
| 2014/0221287 A1 | 8/2014 | Sun et al. | |
| 2014/0256621 A1 | 9/2014 | Erickson et al. | |
| 2017/0051032 A1* | 2/2017 | Raleigh | A61K 38/22 |
| 2019/0134159 A1 | 5/2019 | Mathiesen et al. | |
| 2020/0115430 A1 | 4/2020 | Blackwell et al. | |
| 2020/0188485 A1 | 6/2020 | Mathiesen et al. | |

FOREIGN PATENT DOCUMENTS

| WO | 2007/104789 | | 9/2007 |
| WO | 2009/034119 | | 3/2009 |
| WO | 2010/046357 | | 4/2010 |
| WO | 2020/225781 | A1 | 11/2020 |
| WO | 2022/063925 | A1 | 3/2022 |

OTHER PUBLICATIONS

International Search Report and Written Opinion in International Application No. PCT/US2022/018434, dated Jul. 15, 2022, 14 pages.

* cited by examiner

*Primary Examiner* — Maury A Audet
(74) *Attorney, Agent, or Firm* — Megan Fuller

(57) ABSTRACT

The present disclosure relates to the field of medicine. More particularly, the disclosure is in the field of treatment of diabetes, obesity and/or chronic weight management, dyslipidemia and/or NASH. The disclosure relates to compounds that agonize the amylin receptor and can lower food intake, body weight, glucose and/or triglycerides, so can be used to treat diabetes, obesity, and/or dyslipidemia. The present disclosure also includes pharmaceutical compositions containing such compounds and therapeutic uses of such compounds and compositions.

20 Claims, No Drawings
Specification includes a Sequence Listing.

LONG ACTING AMYLIN RECEPTOR AGONISTS AND USES THEREOF

The present disclosure relates to the field of medicine. More particularly, the present disclosure is in the field of treatment of diabetes, obesity and/or chronic weight management, dyslipidemia and/or non-alcoholic steatohepatitis (NASH). The disclosure relates to compounds that agonize the amylin receptor and can therefore lower food intake, body weight, glucose, HbA1c (glycated hemoglobin), and/or triglycerides, and may be used to treat diabetes, obesity and/or chronic weight management, dyslipidemia, and/or NASH. The present disclosure also includes pharmaceutical compositions containing such compounds and therapeutic uses of such compounds and pharmaceutical compositions.

Over the past several decades, the prevalence of diabetes has continued to rise. Type 2 diabetes mellitus ("T2DM") is the most common form of diabetes, accounting for 90% of all diabetes. T2DM is characterized by high blood glucose levels and associated mainly with insulin resistance. Desired treatments for patients with diabetes should reduce blood glucose and stabilize HbA1c.

Obesity is a complex medical disorder resulting in excessive accumulation of adipose tissue mass. Today, obesity is a global public health concern that is often associated with undesired health outcomes and morbidities. Desired treatments for patients with obesity should reduce excess body weight, improve obesity-related co-morbidities, and/or maintain long-term weight reduction.

Dyslipidemia is an abnormal level of cholesterol and other lipids, also called fats, in the blood. Dyslipidemia increases the chance of clogged arteries (atherosclerosis) and heart attacks, stroke, or other circulatory concerns, especially in individuals who smoke.

NASH stands for non-alcoholic steatohepatitis. It is the liver manifestation of a metabolic disorder and is the most severe form of non-alcoholic fatty liver disease (NAFLD). NASH is closely related to the co-morbidities of diabetes and obesity.

Amylin is a 37 amino acid peptide hormone that is co-secreted with insulin from pancreatic β-cells and is deficient in people with diabetes. It inhibits glucagon secretion, delays gastric emptying and acts as a satiety agent. Consequently, amylin helps regulate the amount of glucose in the body after meals. However, the physiochemical properties of human amylin make its use as a pharmaceutical drug difficult. For example, amylin is difficult to formulate as it is chemically unstable and it precipitates at physiologic pH, necessitating its formulation in acidic solution. Further, the half-life of this medicine is less than an hour and it is used at mealtimes, so a patient would need multiple doses in one day to use this medicine in therapy.

Pramlintide is a commercially available amylin agonist peptide used for the treatment of diabetes as an add-on to insulin. Pramlintide is chemically unstable at neutral pH due to both the presence of a disulfide bond (—S—S—) and deamidation. It is therefore provided in an acidic formulation. Compared to human amylin, the amino acids in position 25, 28, and 29 in pramlintide are substituted with proline. These modifications reduce the peptide's tendency toward fibrillogenesis. However, pramlintide still has a very short plasma half-life and therefore must be injected two to three times daily, which can lead to inconvenience and poor compliance, and subsequently incomplete or less than optimal efficacy. In addition, its low pH formulation is not compatible with neutral pH formulation used for insulin and GLP-1 analogs, which makes its co-administration with such compounds, which could have synergistic and thus improved clinical efficacy, complicated.

Human amylin binds to two distinct receptor complexes. These two complexes also contain the calcitonin receptor plus receptor activity proteins, RAMP1 or RAMP3. The calcitonin receptor is found in many tissues throughout the body, and it is believed to be involved in regulation of bone metabolism. However, apart from bone regulation, very little is known about the physiology of calcitonin receptors in humans, and thus, the risk of off-target toxicity may be increased with a molecule with high affinity for calcitonin receptors. It is therefore believed that amylin-based polypeptides that have an increased selectivity for the amylin receptor compared to the calcitonin receptor could offer an advantageous pharmacokinetic and pharmacological profile.

From the close relationship between the calcitonin receptor and the amylin receptor, some cross-reactivity to the calcitonin receptor may be expected of amylin receptor agonists. As an example, pramlintide, an amylin agonist peptide, has some affinity to the calcitonin receptor, though it is 14 times more potent on the amylin receptor.

Polypeptides comprising human amylin agonist peptides and having an albumin binding moiety have been disclosed. See WO 2010/046357, WO 2009/034119, and WO 2007/104789. Even though these polypeptides with albumin binding moieties show improved pharmacokinetic (PK) or pharmacodynamic (PD) properties compared to pramlintide, they may still show poor physical stability under certain conditions. In addition, the polypeptides generally do not show selectivity for the amylin receptor over the calcitonin receptor. US2014/0087995 relates to polypeptides comprising amylin agonist peptides with selectivity for the amylin receptor over the calcitonin receptor. However, there remains a need for amylin agonist peptide drug candidates with higher potency, lower developability risk, lower immunogenicity risk, improved chemical stability, and compatibility with formulation at a neutral pH.

There is a need for compounds (e.g., peptides) that show selectivity for agonism of the amylin receptor over the calcitonin receptor. In addition, the need exists for amylin receptor agonists with extended time of action and preserved potency. Therapeutically desirable compounds would agonize the amylin receptor and provide one or more advantageous properties such as lowering any of the following: food intake, body weight, blood glucose levels, HbA1c, triglycerides, and/or insulin levels. In addition, therapeutically desirable compounds may have one or more additional advantageous properties such as extended time of action with preserved or improved potency in agonizing the amylin receptor, a low risk of immunogenic response, and/or a low risk of fibrillation.

Further, combination of an amylin receptor agonist of the present disclosure, optionally combined with an incretin or incretin analog, is desired to provide treatment for diabetes, obesity, NASH, and/or dyslipidemia. Such combination will also preferably be more effective than either molecule alone. For example, such treatment with such combination may allow for use of lower doses of either or both molecules as compared to each molecule alone, potentially leading to lower side effects (or a shorter duration of one or the other therapy) while maintaining efficacy. It is believed that the novel combination(s) provided herein will be effective treatments for diabetes, obesity, NASH, and/or dyslipidemia.

Accordingly, the present disclosure provides a method of treating diabetes, obesity, NASH, and/or dyslipidemia, comprising administering to a patient in need of such treatment an effective amount of an amylin receptor agonist of the present invention and an effective amount of an additional agent.

Accordingly, the present disclosure recites novel compounds (peptides) that agonize the amylin receptor and have one or more of the following properties: (1) effective reduction in food intake and body weight; (2) glucose and insulin lowering; (3) decreased risk of immunogenicity and a low risk of fibrillation compared to pramlintide; (4) greatly extended half-life compared to pramlintide. Extended half-life of the presently disclosed compounds will enable once-weekly dosing of these compounds for use in therapy.

One embodiment of the present disclosure is a compound comprising: $Xaa_1$-C-$Xaa_3$-TATCAT-$Xaa_{10}$-$Xaa_{11}$-$Xaa_{12}$-AE-$Xaa_{15}$-LVRSS-$Xaa_{21}$-$Xaa_{22}$-FGP-$Xaa_{26}$-LPPTEVG-SNTY-$NH_2$, wherein $Xaa_1$ is K or γE; $Xaa_3$ is E, N, or G; $Xaa_{10}$ is G or Q; $Xaa_{11}$ is Orn or K; $Xaa_{12}$ is L or αMeL; $Xaa_{15}$ is αMeF or F; $Xaa_{21}$ is N or H; $Xaa_{22}$ is NMeD, NMeN, or N; $Xaa_{26}$ is I or K, or a pharmaceutical acceptable salt thereof (SEQ ID NO:14). Optionally, the compounds comprising SEQ ID NO:14 further comprise an additional element to extend the time action profile of this compound. These additional elements include, with or without a linker and at any suitable position in the sequence, the Fc portion of an immunoglobulin, fragments of the Fc portion of the immunoglobulin, human serum albumin (HSA), a variant of VHH (variable domain of heavy chain antibodies)), nanobody, fragments of human serum albumin, $C_{20}$ monoacid, a $C_{20}$ diacid, and a polyethylene glycol (PEG) moiety or other types of high molecular weight polymer. Preferably, the additional element is attached optionally with a linker to a lysine on the compound. Further, in any of the embodiments disclosed herein, the amylin agonist peptides and compounds comprising the amylin agonist peptides, may further comprise such elements, either in addition to any elements already present that are attached or linked to the peptide sequence and that extend the time action profile, or as an alternative to an existing element.

In some embodiments of the compounds of comprising SEQ ID NO:14, $Xaa_{26}$ is lysine. In some embodiments of the compounds comprising SEQ ID NO:14, the lysine at position 26, if present, is attached to a fatty acid via a linker according to the formula: $(γE)_2$-CO—$(CH_2)_{18}$—$CO_2H$. In some embodiments of the compounds comprising SEQ ID NO:14, the lysine at position 26, if present, is attached to a fatty acid via a linker according to the formula: $AEEA_2$-γE-CO—$(CH_2)_{18}$—$CO_2H$. In some embodiments of the compounds comprising SEQ ID NO:14, the lysine at position 26, if present, is attached to a fatty acid via a linker according to the formula: γE-$AEEA_2$-CO—$(CH_2)_{18}$—$CO_2H$. In some embodiments of the compounds comprising SEQ ID NO: 14, the lysine at position 26, if present, is attached to a fatty acid via a linker according to the formula: $(γE)_2$-AEEA-CO—$(CH_2)_{18}$—$CO_2H$. In other embodiments of the compounds comprising SEQ ID NO:14, the lysine at position 26, if present, is attached to a fatty acid via another linker known in the art. Further, in any of the embodiments disclosed herein, the amylin agonist peptides and compounds comprising the amylin agonist peptides may comprise another linker to attach the fatty acid according to the formulas herein.

In some embodiments of the compounds comprising SEQ ID NO:14, $Xaa_1$ is lysine. In some embodiments of the compounds comprising SEQ ID NO:14, the lysine at position 1, if present, is attached to a fatty acid via a linker according to the formula: $(γE)_2$-CO—$(CH_2)_{18}$—$CO_2H$. In other embodiments of the compounds comprising SEQ ID NO:14, the lysine at position 1, if present, is attached to a fatty acid via another linker known in the art.

In some embodiments of the compounds comprising SEQ ID NO:14, there is a disulfide bridge between the cysteines at positions 2 and 7. In a preferred embodiment of the compounds comprising SEQ ID NO:14, there is a thioacetal bridge between the cysteines at positions 2 and 7.

One of the embodiments herein comprises the following sequence: γE-CNTATCATG-Orn-LAE-αMeF-LVRSSN-NMeN-FGPKLPPTEVGSNTY-$NH_2$ (SEQ ID NO:1). An alternative embodiment herein consists of the following sequence: γE-CNTATCATG-Orn-LAE-αMeF-LVRSSN-NMeN-FGPKLPPTEVGSNTY-$NH_2$ (SEQ ID NO:1). Below is a depiction of Compound I using the standard single letter amino acid codes with the exception of the glutamic acid (γE) at position 1 (where the peptide bond is formed using its side chain carboxylic acid group at the gamma position rather than the typical alpha position), the cysteines at positions 2 and 7, Orn at position 11, αMeF at position 15, NMeN at position 22, and tyrosine at position 37, where the structures of these amino acid residues have been expanded:

Compound I; SEQ ID NO: 1

-continued

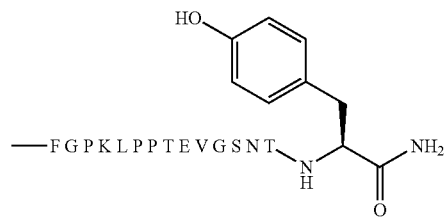

Alternatively, the compound can have at least about 90% to about 99% sequence similarity to SEQ ID NO:1. Alternatively, the compound can have at least about 90%, 91%, 92%, 93%, 94%, 95%, 96%, 97%, 98%, or 99% sequency similarity to SEQ ID NO:1.

In some embodiments of the compounds comprising SEQ ID NO:1, the lysine at position 26 is attached to a fatty acid via a linker. In a preferred embodiment of the compounds comprising SEQ ID NO:1, the lysine at position 26 is attached to a fatty acid via a linker according to the formula: $(\gamma E)_2$-CO—$(CH_2)_{18}$—$CO_2H$.

One of the embodiments herein comprises the following sequence: γE-CNTATCATG-Orn-LAE-αMeF-LVRSSN-NMeN-FGPKLPPTEVGSNTY-$NH_2$, wherein there is a thioacetal bridge between the cysteines at positions 2 and 7, and wherein the lysine at position 26 is attached to a fatty acid via a linker according to the formula: $(\gamma E)_2$-CO—$(CH_2)_{18}$—$CO_2H$ (SEQ ID NO:2). An alternative embodiment herein consists of the following sequence: γE-CNTATCATG-Orn-LAE-αMeF-LVRSSN-NMeN-FGPKLPPTEVGSNTY-$NH_2$, wherein there is a thioacetal bridge between the cysteines at positions 2 and 7, and wherein the lysine at position 26 is attached to a fatty acid via a linker according to the formula: $(\gamma E)_2$-CO—$(CH_2)_{18}$—$CO_2H$ (SEQ ID NO:2). Below is a depiction of Compound II using the standard single letter amino acid codes with the exception of the glutamic acid (γE) at position 1 (where the peptide bond is formed using its side chain carboxylic acid at the gamma position rather than the typical alpha position), the cysteines at positions 2 and 7, Orn at position 11, αMeF at position 15, NMeN at position 22, lysine at position 26, and tyrosine at position 37 where the structures of these amino acid residues have been expanded:

Compound II; SEQ ID NO: 2

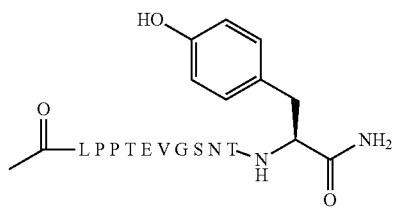

Alternatively, the compound can have at least about 90% to about 99% sequence similarity to SEQ ID NO:2. Alternatively, the compound can have at least about 90%, 91%, 92%, 93%, 94%, 95%, 96%, 97%, 98%, or 99% sequency similarity to SEQ ID NO:2.

One of the embodiments herein comprises the following sequence: γE-CNTATCATG-Orn-LAE-αMeF-LVRSSN-NMeD-FGPKLPPTEVGSNTY-NH$_2$ (SEQ ID NO:3). An alternative embodiment herein consists of the following sequence: γE-CNTATCATG-Orn-LAE-αMeF-LVRSSN-NMeD-FGPKLPPTEVGSNTY-NH$_2$ (SEQ ID NO:3). Below is a depiction of Compound III using the standard single letter amino acid codes with the exception of the glutamic acid (γE) at position 1 (wherein the peptide bond is formed using its side chain carboxylic acid group at the gamma position rather than the typical alpha position), the cysteines at positions 2 and 7, Orn at position 11, αMeF at position 15, NMeD at position 22, and tyrosine at position 37 where the structures of these amino acid residues have been expanded:

comprising SEQ ID NO:3, the lysine at position 26 is attached to a fatty acid linker moiety of the formula: (γE)$_2$-CO—(CH$_2$)$_{18}$—CO$_2$H.

One of the embodiments herein comprises the following sequence: γE-CNTATCATG-Orn-LAE-αMeF-LVRSSN-NMeD-FGPKLPPTEVGSNTY-NH$_2$, wherein there is a thioacetal bridge between the cysteines at positions 2 and 7, and wherein the lysine at position 26 is attached to a fatty acid linker moiety according to the formula: (γE)$_2$-CO—(CH$_2$)$_{18}$—CO$_2$H (SEQ ID NO:4). An alternative embodiment herein consists of the following sequence: γE-CNTAT-CATG-Orn-LAE-αMeF-LVRSSN-NMeD-FGPKLPPTEVGSNTY-NH$_2$, wherein there is a thioacetal bridge between the cysteines at positions 2 and 7, and wherein the lysine at position 26 is attached to a fatty acid linker moiety according to the formula: (γE)$_2$-CO—(CH$_2$)$_{18}$—CO$_2$H (SEQ ID NO:4). Below is a depiction of Compound IV using the standard single letter amino acid codes Compound III; SEQ ID NO: 3

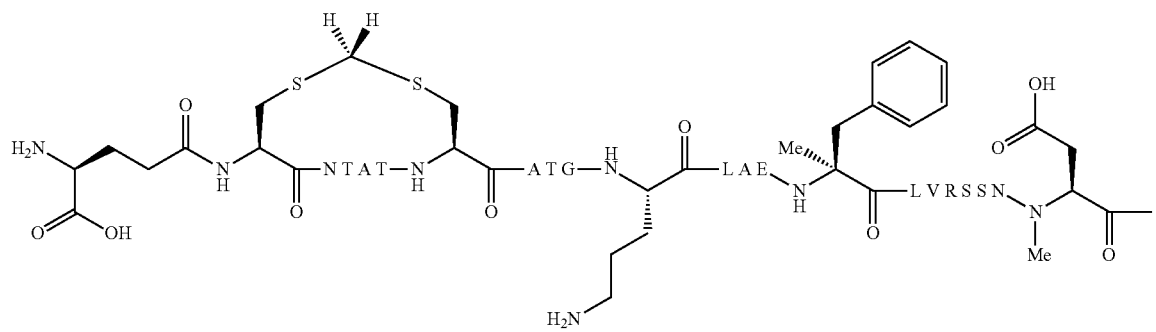

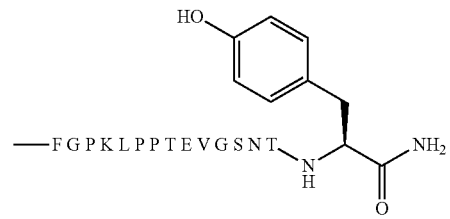

Alternatively, the compound can have at least about 90% to about 99% sequence similarly to SEQ ID NO:3. Alternatively the compound can have at least about 90%, 91%, 92%, 93%, 94%, 95%, 96%, 97%, 98%, or 99% sequency similarity to Compound III (SEQ ID NO:3).

In some embodiments of the compounds comprising SEQ ID NO:3, the lysine at position 26 is attached to a fatty acid via a linker. In a preferred embodiment of the compounds with the exception of the glutamic acid (γE) at position 1 (where the peptide bond is formed using its side chain carboxylic acid group at the gamma position rather than the typical alpha position), the cysteines at positions 2 and 7, Orn at position 11, αMeF at position 15, NMeD at position 22, lysine at position 26, and tyrosine at position 37 where the structures of these amino acid residues have been expanded:

Compound IV; SEQ ID NO: 4

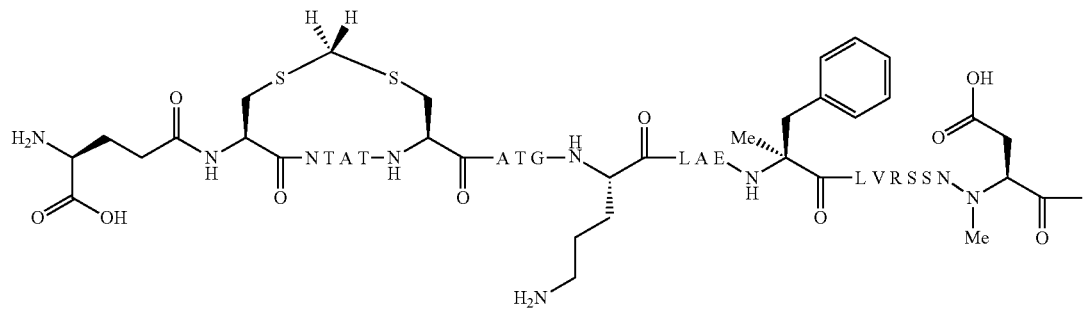

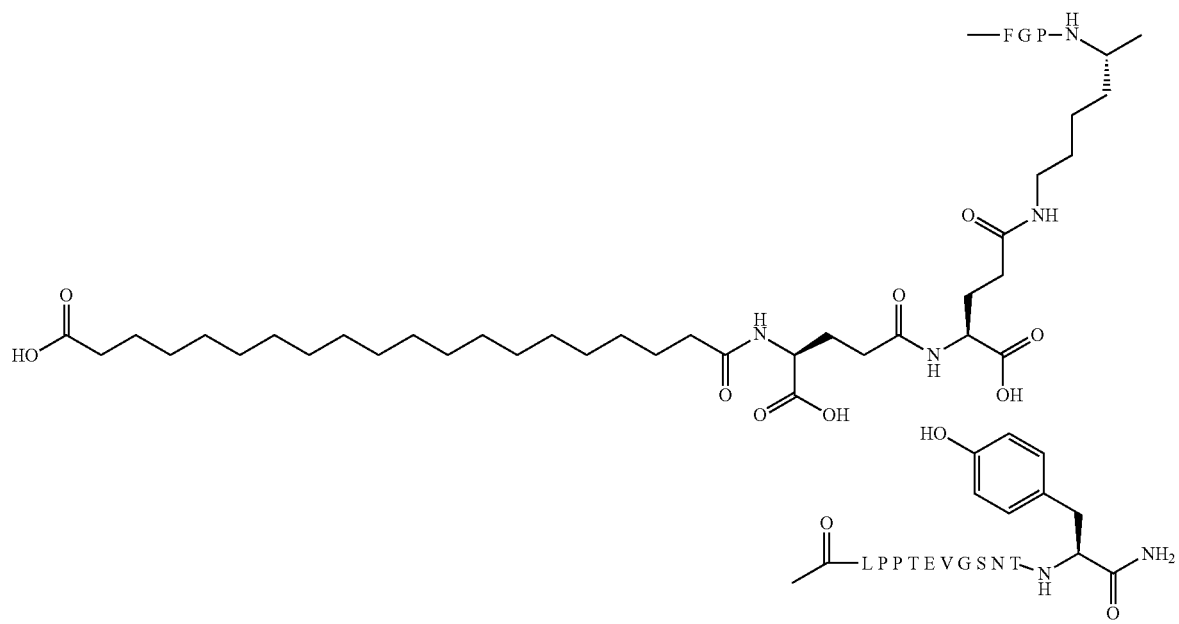

Alternatively, the compound can have at least about 90% to about 99% sequence similarity to SEQ ID NO:4. Alternatively, the compound can have at least about 90%, 91%, 92%, 93%, 94%, 95%, 96%, 97%, 98%, or 99% sequency similarity to SEQ ID NO:4.

One of the embodiments herein comprises the following sequence: KCETATCATG-Orn-LAE-αMeF-LVRSSN-NMeD-FGPILPPTEVGSNTY-NH₂ (SEQ ID NO:5). An alternative embodiment herein consists of the following sequence: KCETATCATG-Orn-LAE-αMeF-LVRSSN-NMeD-FGPILPPTEVGSNTY-NH₂ (SEQ ID NO:5). Below is a depiction of Compound V using the standard single letter amino acid codes with the exception of cysteines at positions 2 and 7, Orn at position 11, αMeF at position 15, NMeD at position 22, and tyrosine at position 37 where the structures of these amino acid residues have been expanded:

Compound V; SEQ ID NO: 5

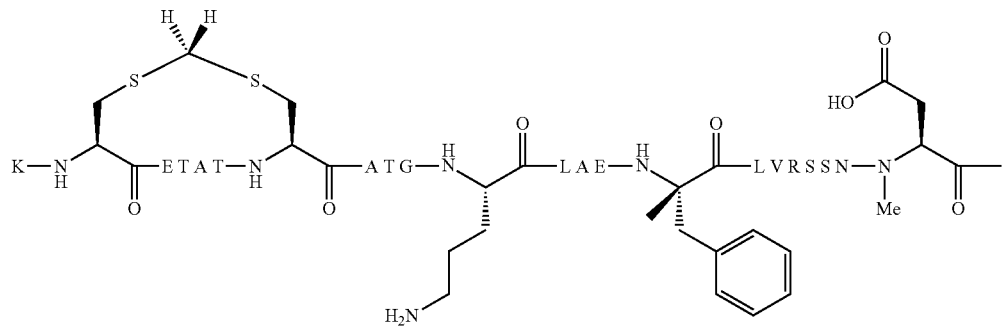

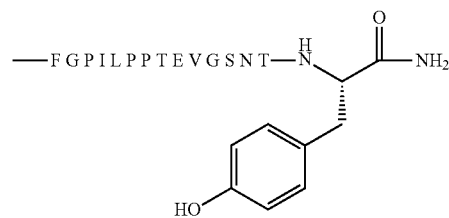

Alternatively, the compound can have at least about 90% to about 99% sequence similarity to SEQ ID NO:5. Alternatively, the compound can have at least about 90%, 91%, 92%, 93%, 94%, 95%, 96%, 97%, 98%, or 99% sequency similarity to SEQ ID NO:5.

In some embodiments of the compounds comprising SEQ ID NO:5, the lysine at position 1 is attached to a fatty acid via a linker. In a preferred embodiment of the compounds comprising SEQ ID NO:5, the lysine at position 1 is attached to a fatty acid via a linker according to the formula: $(\gamma E)_2\text{-CO}\text{-}(CH_2)_{18}\text{-}CO_2H$.

cysteines at positions 2 and 7, and wherein the lysine at position 1 is attached to a fatty acid linker moiety according to the formula: $(\gamma E)_2\text{-CO}\text{-}(CH_2)_{18}\text{-}CO_2H$ (SEQ ID NO:6). Below is a depiction of Compound VI using the standard single letter amino acid codes with the exceptions of the lysine at position 1, the cysteines at positions 2 and 7, Orn at position 11, αMeF at position 15, NMeD at position 22, and tyrosine at position 37 where the structures of these amino acid residues have been expanded:

Compound VI; SEQ ID NO: 6

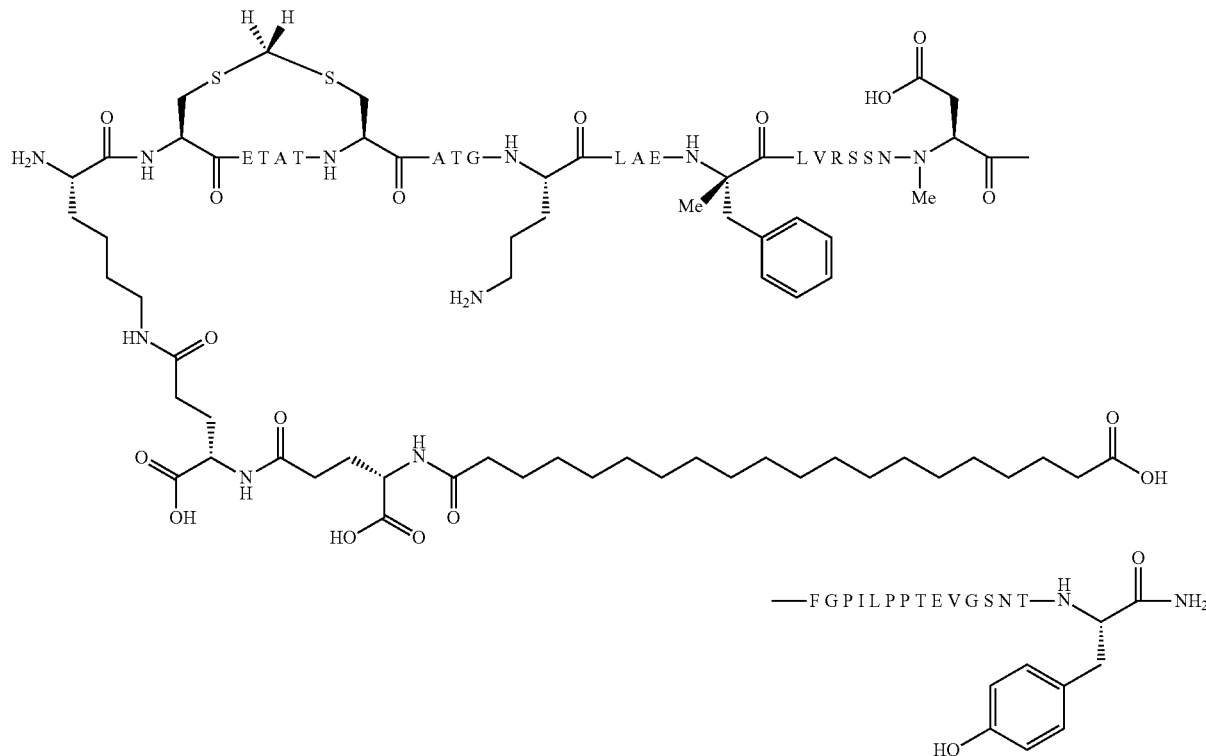

One of the embodiments herein comprises the following sequence: KCETATCATG-Orn-LAE-αMeF-LVRSSN-NMeD-FGPILPPTEVGSNTY-NH$_2$, wherein there is a thioacetal bridge between the cysteines at positions 2 and 7, and wherein the lysine at position 1 is attached to a fatty acid linker moiety according to the formula: $(\gamma E)_2\text{-CO}\text{-}(CH_2)_{18}\text{-}CO_2H$ (SEQ ID NO:6). An alternative embodiment herein consists of the following sequence: KCETATCATG-Orn-LAE-αMeF-LVRSSN-NMeD-FGPILPPTEVGSNTY-NH$_2$, wherein there is a thioacetal bridge between the Alternatively, the compound can have at least about 90% to about 99% sequence similarity to SEQ ID NO:6. Alternatively, the compound can have at least about 90%, 91%, 92%, 93%, 94%, 95%, 96%, 97%, 98%, or 99% sequency similarity to Compound VI (SEQ ID NO:6).

One of the embodiments herein comprises the following sequence: KCETATCATG-Orn-αMeL-AEFLVRSSHNFG-PILPPTEVGSNTY-NH$_2$ (SEQ ID NO:7). An alternative embodiment herein consists of the following sequence: KCETATCATG-Orn-αMeL-AEFLVRSSHNFGPILPPTE- VGSNTY-NH$_2$ (SEQ ID NO:7). Below is a depiction of Compound VII with the exception of the cysteines at positions 2 and 7, Orn at position 11, αMeL at position 12, and tyrosine at position 37 where the structures of these amino acid residues have been expanded:

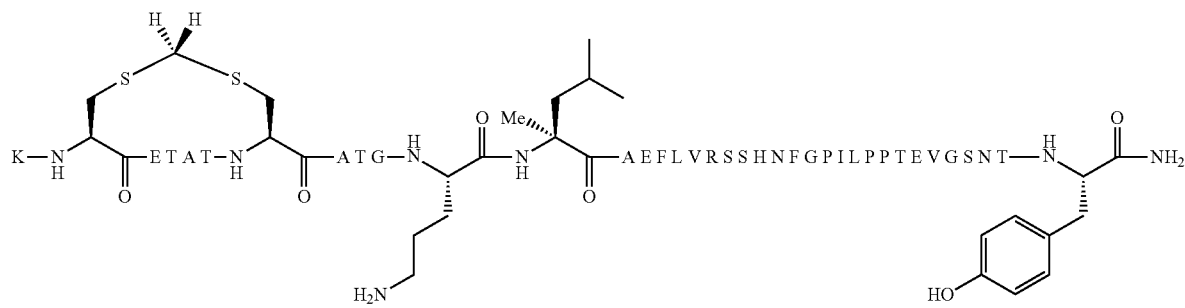

Compound VII; SEQ ID NO: 7

Alternatively, the compound can have at least about 90% to about 99% sequence similarity to SEQ ID NO:7. Alternatively, the compound can have at least about 90%, 91%, 92%, 93%, 94%, 95%, 96%, 97%, 98%, or 99% sequency similarity to SEQ ID NO:7.

In some embodiments of the compounds comprising SEQ ID NO:7, the lysine at position 1 is attached to a fatty acid linker moiety. In a preferred embodiment of the compounds comprising SEQ ID NO:7, the lysine at position 1 is attached to a fatty acid via a linker according to the formula: (γE)$_2$-CO—(CH$_2$)$_{18}$—CO$_2$H.

One of the embodiments herein comprises the following sequence: KCETATCATG-Orn-αMeL-AEFLVRSSHNFG-PILPPTEVGSNTY-NH$_2$, wherein there is a thioacetal bridge between the cysteines at positions 2 and 7, and wherein the lysine at position 1 is attached to a fatty acid via a linker according to the formula: (γE)$_2$-CO—(CH$_2$)$_{18}$—CO$_2$H (SEQ ID NO:8). An alternative embodiment herein consists of the following sequence: KCETATCATG-Orn-αMeL-AEFLVRSSHNFGPILPPTEVGSNTY-NH$_2$, wherein there is a thioacetal bridge between the cysteines at positions 2 and 7, and wherein the lysine at position 1 is attached to a fatty acid via a linker according to the formula: (γE)$_2$-CO—(CH$_2$)$_{18}$—CO$_2$H (SEQ ID NO:8). Below is a depiction of Compound VIII using the standard single letter amino acid codes with the exception of the lysine at position 1, the cysteines at positions 2 and 7, Orn at position 11, αMeL at position 12, and tyrosine at position 37 where the structures of these amino acid residues have been expanded:

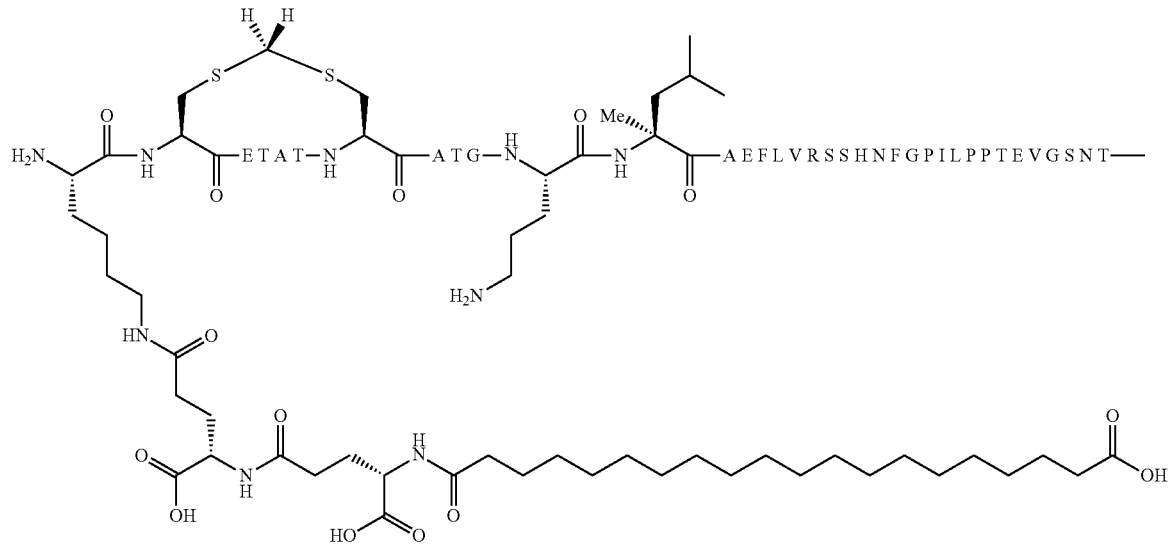

Compound VIII; SEQ ID NO: 8

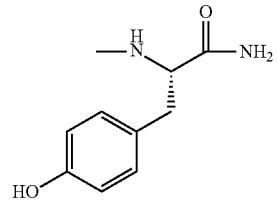

Alternatively, the compound can have at least about 90% to about 99% sequence similarity to SEQ ID NO:8. Alternatively, the compound can have at least about 90%, 91%, 92%, 93%, 94%, 95%, 96%, 97%, 98%, or 99% sequency similarity to SEQ ID NO:8.

chain carboxylic acid group at the gamma position rather than the typical alpha position), the cysteines at positions 2 and 7, lysine at position 26, and tyrosine at position 37 where the structures of these amino acid residues have been expanded:

Compound IX; SEQ ID NO: 9

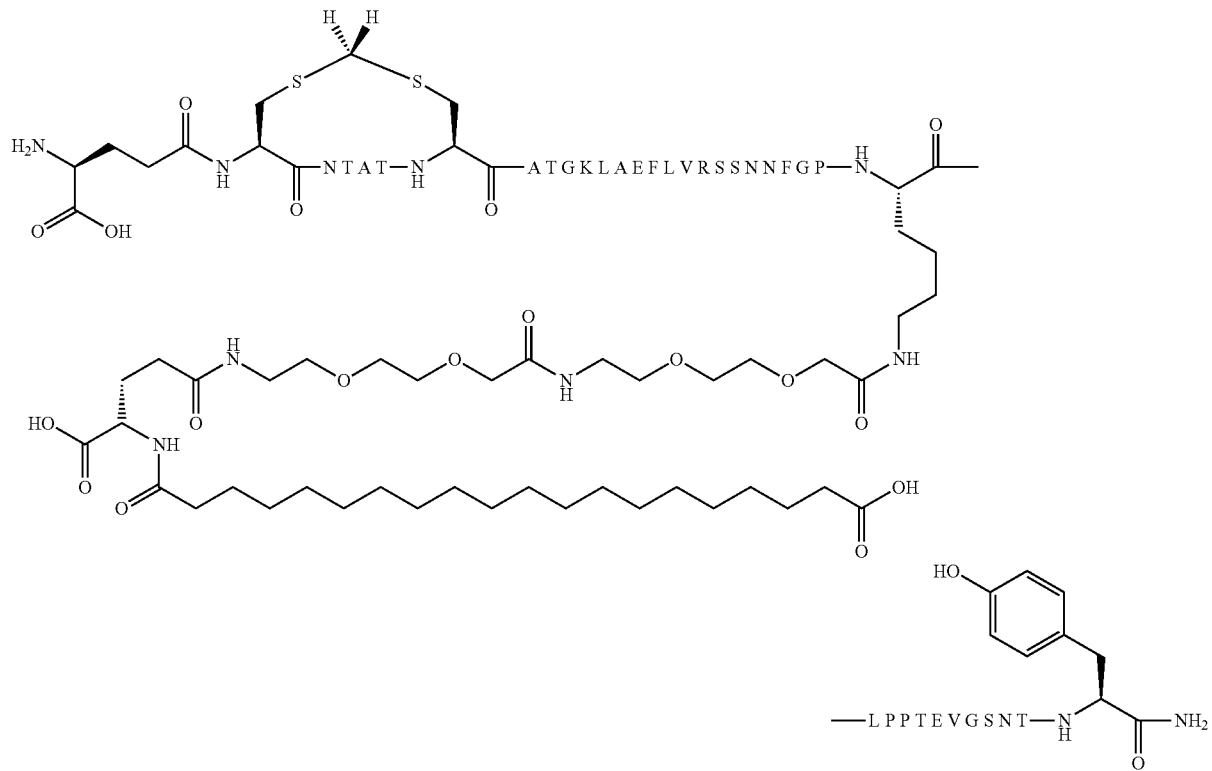

One of the embodiments herein comprises the following sequence: γE-CNTATCATGKLAEFLVRSSNNFGPKL PPTEVGSNTY-NH$_2$, wherein there is a thioacetal bridge between the cysteines at positions 2 and 7, and wherein the lysine at position 26 is attached to a fatty acid via a linker according to the formula: AEEA$_2$-γE-CO—(CH$_2$)$_{18}$—CO$_2$H (SEQ ID NO:9). An alternative embodiment herein consists of the following sequence: γE-CNTATCATGKLAE-FLVRSSNNFGPKLPPTEVGSNTY-NH$_2$, wherein there is a thioacetal bridge between the cysteines at positions 2 and 7, and wherein the lysine at position 26 is attached to a fatty acid via a linker according to the formula: AEEA$_2$-γE-CO—(CH$_2$)$_{18}$—CO$_2$H (SEQ ID NO:9) Below is a depiction of Compound IX using the standard single letter amino acid codes with the exception of the glutamic acid (γE) at position 1 (where the peptide bond is formed using its side Alternatively, the compound can have at least about 90% to about 99% sequence similarity to SEQ ID NO:9. Alternatively, the compound can have at least about 90%, 91%, 92%, 93%, 94%, 95%, 96%, 97%, 98%, or 99% sequency similarity to SEQ ID NO:9.

One of embodiments herein comprises the following sequence: γE-CNTATCATGKLAEFLVRSSNNFGP KLPPTEVGSNTY-NH$_2$, wherein there is a thioacetal bridge between the cysteines at positions 2 and 7, and wherein the lysine at position 26 is attached to a fatty acid via a linker according to the formula: γE-AEEA$_2$-CO—(CH$_2$)$_{18}$—CO$_2$H (SEQ ID NO:10). An alternative embodiment herein consists of the following sequence: γE-CNTATCATGK-LAEFLVRSSNNFGPKLPPTEVGSNTY-NH$_2$, wherein there is a thioacetal bridge between the cysteines at positions 2 and 7, and wherein the lysine at position 26 is attached to a fatty acid via a linker according to the formula: γE-AEEA$_2$-CO—(CH$_2$)$_{18}$—CO$_2$H (SEQ ID NO:10). Below is a depiction of Compound X using the standard single letter amino acid codes with the exception of the glutamic acid (γE) at position 1 (where the peptide bond is formed using its side chain carboxylic acid group at the gamma position rather than the typical alpha position), the cysteines at positions 2 and 7, lysine at position 26, and tyrosine at position 37 where the structures of these amino acid residues have been expanded:

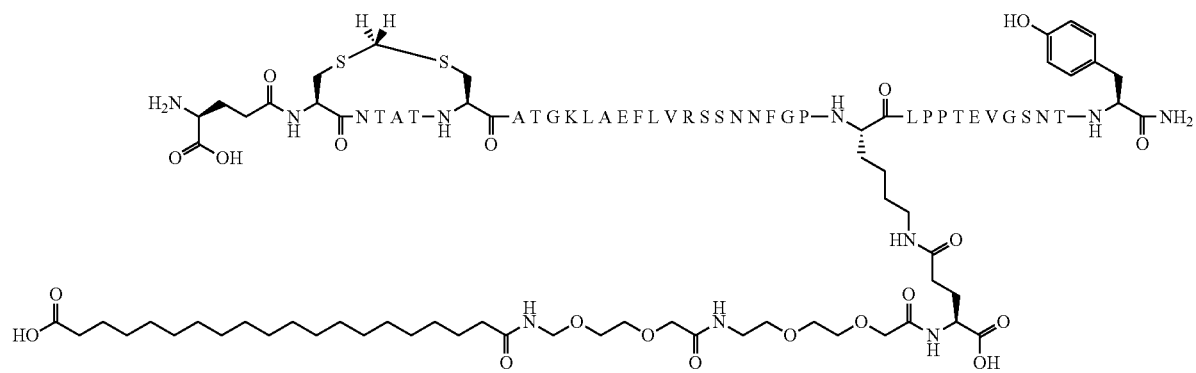

Compound X; SEQ ID NO: 10

Alternatively, the compound can have at least about 90% to about 99% sequence similarity to SEQ ID NO:10. Alternatively, the compound can have at least about 90%, 91%, 92%, 93%, 94%, 95%, 96%, 97%, 98%, or 99% sequency similarity to SEQ ID NO:10.

One of the embodiments herein comprises the following sequence: γE-CNTATCATGKLAEFLVRSSNNFGPKLPPT EVGSNTY-NH$_2$, wherein there is a thioacetal bridge between the cysteines at positions 2 and 7, and wherein the lysine at position 26 is attached to a fatty acid linker moiety according to the formula: (γE)$_2$-AEEA-CO—(CH$_2$)$_{18}$—CO$_2$H (SEQ ID NO:11). An alternative embodiment herein consists of the following sequence: γE-CNTATCATGK-LAEFLVRSSNNFGPKLPPTEVGSNTY-NH$_2$, wherein there is a thioacetal bridge between the cysteines at positions 2 and 7, and wherein the lysine at position 26 is attached to a fatty acid linker moiety according to the formula: (γE)$_2$-AEEA-CO—(CH$_2$)$_{18}$—CO$_2$H (SEQ ID NO:11). Below is a depiction of Compound XI using the standard single letter amino acid codes with the exception of the glutamic acid (γE) at position 1 (where the peptide bond is formed using its side chain carboxylic acid group at the gamma position rather than the typical alpha position), the cysteines at positions 2 and 7, lysine at position 26, and tyrosine at position 37 where the structures of these amino acid residues have been expanded:

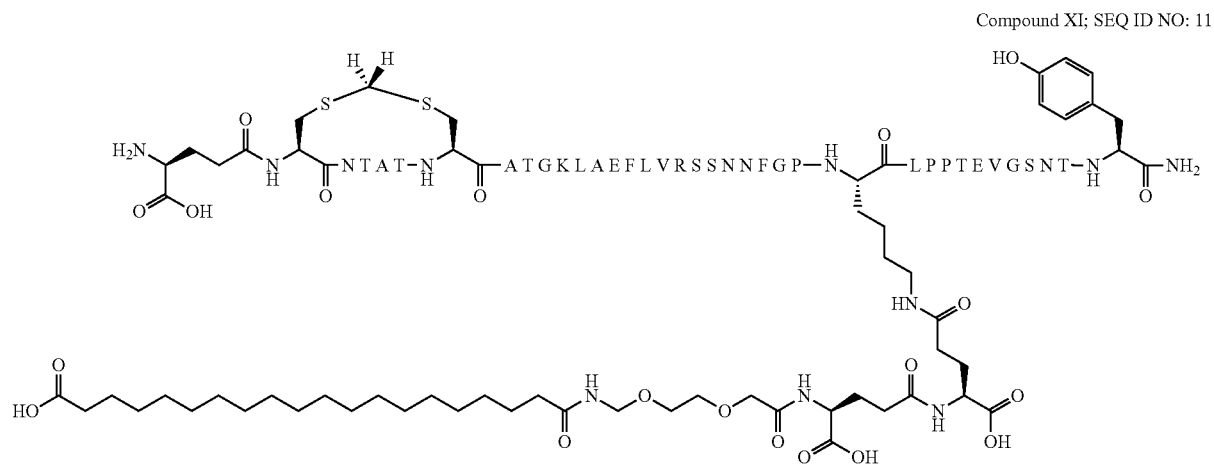

Compound XI; SEQ ID NO: 11

Alternatively, the compound can have at least about 90% to about 99% sequence similarity to SEQ ID NO:11. Alternatively, the compound can have at least about 90%, 91%, 92%, 93%, 94%, 95%, 96%, 97%, 98%, or 99% sequency similarity to SEQ ID NO:11.

One of the embodiments herein comprises the following sequence: γE-CNTATCATQ-Orn-LAEFLVRSSNNFGPKLPPTEVGSNTY-NH$_2$, wherein there is a thioacetal bridge between the cysteines at positions 2 and 7, and wherein the lysine at position 26 is attached to a fatty acid via a linker according to the formula: AEEA$_2$-γE-CO—(CH$_2$)$_{18}$—CO$_2$H (SEQ ID NO:12). An alternative embodiment consists of the following sequence: γE-CNTATCATQ-Orn-LAEFLVRSSNNFGPKLPPTEVGSNTY-NH$_2$, wherein there is a thioacetal bridge between the cysteines at positions 2 and 7, and wherein the lysine at position 26 is attached to a fatty acid via a linker according to the formula: AEEA$_2$-γE-CO—(CH$_2$)$_{18}$—CO$_2$H (SEQ ID NO:12). Below is a depiction of Compound XII using the standard single letter amino acid codes with the exception of the glutamic acid (γE) at position 1 (where the peptide bond is formed using its side chain carboxylic acid group at the gamma position rather than the typical alpha position), the cysteines at positions 2 and 7, ornithine at position 11, lysine at position 26, and tyrosine at position 37 where the structures of these amino acid residues have been expanded:

Compound 12; SEQ ID NO: 12

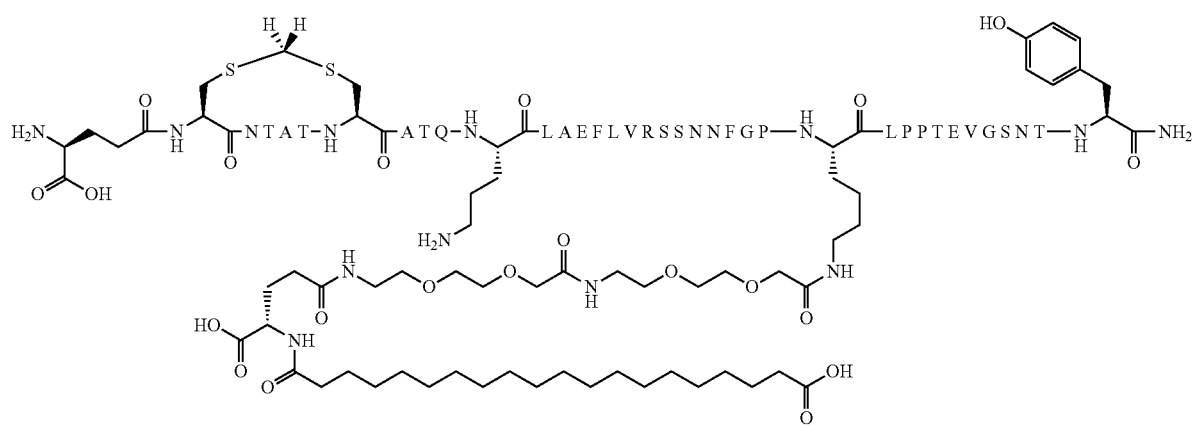

Alternatively, the compound can have at least about 90% to about 99% sequence similarity to SEQ ID NO:12. Alternatively, the compound can have at least about 90%, 91%, 92%, 93%, 94%, 95%, 96%, 97%, 98%, or 99% sequency similarity to SEQ ID NO:12.

One of the embodiments herein comprises the following sequence: γE-CGTATCATG-Orn-LAEFLVRSSNNFGPKLPPTEVGSNTY-NH$_2$, wherein there is a thioacetal bridge between the cysteines at positions 2 and 7, and wherein the lysine at position 26 is attached to a fatty acid linker moiety according to the formula: γE$_2$-CO—(CH$_2$)$_{18}$—CO$_2$H (SEQ ID NO:13). An alternative embodiment herein consists of the following sequence: γE-CGTATCATG-Orn-LAEFLVRSSNNFGPKLPPTEVGSNTY-NH$_2$, wherein there is a thioacetal bridge between the cysteines at positions 2 and 7, and wherein the lysine at position 26 is attached to a fatty acid linker moiety according to the formula: γE$_2$-CO—(CH$_2$)$_{18}$—CO$_2$H (SEQ ID NO:13). Below is a depiction of Compound XIII using the standard single letter amino acid codes with the exception of the glutamic acid (γE) at position 1 (where the peptide bond is formed using its side chain carboxylic acid group at the gamma position rather than the typical alpha position), the cysteines at positions 2 and 7, ornithine at position 11, lysine at position 26, and tyrosine at position 37 where the structures of these amino acid residues have been expanded:

Compoound 13: SEQ ID NO: 13

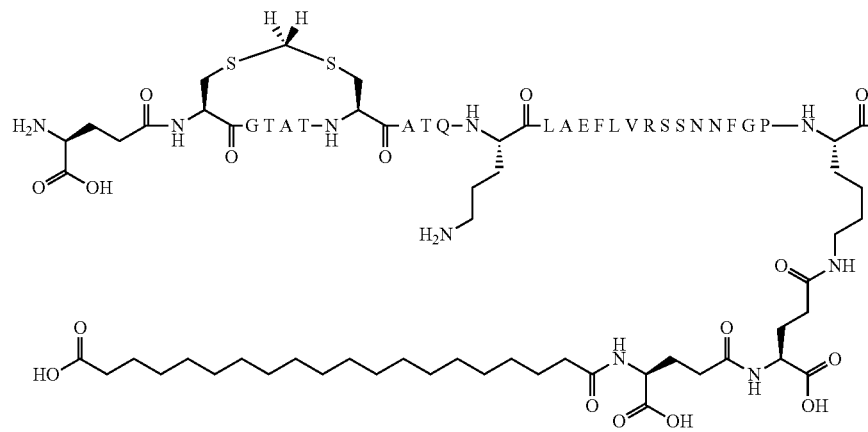

Alternatively, the compound can have at least about 90% to about 99% sequence similarity to SEQ ID NO:13. Alternatively, the compound can have at least about 90%, 91%, 92%, 93%, 94%, 95%, 96%, 97%, 98%, or 99% sequence similarity to SEQ ID NO:13.

The present disclosure provides a compound consisting of SEQ ID NO:1, a compound consisting of SEQ ID NO:2, a compound consisting of SEQ ID NO:3, a compound consisting of SEQ ID NO:4, a compound consisting of SEQ ID NO:5, a compound consisting of SEQ ID NO:6, a compound consisting of SEQ ID NO:7, a compound consisting of SEQ ID NO:8, a compound consisting of SEQ ID NO:9, a compound consisting of SEQ ID NO:10, a compound consisting of SEQ ID NO:11, a compound consisting of SEQ ID NO:12, and/or a compound consisting of SEQ ID NO:13, or a pharmaceutical acceptable salt thereof. The present disclosure also provides a pharmaceutical composition comprising a compound comprising SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, SEQ ID NO:10, SEQ ID NO:11, SEQ ID NO:12, SEQ ID NO:13, or SEQ ID NO:14, or a pharmaceutical acceptable salt thereof, and one or more pharmaceutically acceptable carriers, diluents, or excipients. The present disclosure also provides a pharmaceutical composition comprising a compound consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14, or a pharmaceutical acceptable salt thereof, and one or more pharmaceutically acceptable carriers, diluents, or excipients.

The present disclosure further provides compounds comprising SEQ ID NO:22, SEQ ID NO:23, SEQ ID NO:24, SEQ ID NO:25, or a pharmaceutical acceptable salt thereof. In another embodiment the present disclosure provides compounds consisting of SEQ ID NO:22, SEQ ID NO:23, SEQ ID NO:24, SEQ ID NO:25, or a pharmaceutical acceptable salt thereof. Preferably, the compounds of SEQ ID NO:22, SEQ ID NO:23, SEQ ID NO:24, SEQ ID NO:25 comprise a disulfide or thioacetal bridge between the cysteines at positions 2 and 7. More preferably, the compounds comprising SEQ ID NO:22, SEQ ID NO:23, SEQ ID NO:24, SEQ ID NO:25 have a thioacetal bridge between the cysteines at positions 2 and 7 and attached to a fatty acid linker moiety. Preferably the fatty acid moiety is attached to a lysine.

The present disclosure provides a method of treating diabetes, obesity, dyslipidemia, and/or NASH, in a patient comprising administering to a patient in need thereof an effective amount of the compounds comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14, or a pharmaceutical acceptable salt thereof, or pharmaceutical compositions comprising the same. The present disclosure further provides a method of lowering food intake, lowering body weight, lowering blood glucose, lowering HbA1c, and/or lowering triglycerides comprising administering to a patient in need thereof an effective amount of the compounds comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO: 9, SEQ ID NO:10, SEQ ID NO:11, SEQ ID NO:12, SEQ ID NO:13, or SEQ ID NO:14, or a pharmaceutical acceptable salt thereof, or pharmaceutical compositions comprising the same. Preferably, the present disclosure provides a method of treating diabetes, obesity, dyslipidemia, and/or NASH, in a patient comprising administering to a patient in need thereof an effective amount of the compounds comprising SEQ ID NO:2, or pharmaceutical compositions comprising the same. More preferably, the present disclosure provides a method of treating diabetes in a patient, comprising administering to a patient in need thereof an effective amount of the compounds comprising SEQ ID NO:2, or pharmaceutical compositions comprising the same. Alternatively, the present disclosure provides a method of treating obesity in a patient, comprising administering to a patient in need thereof an effective amount of the compounds comprising SEQ ID NO:2, or pharmaceutical compositions comprising the same.

The present application provides the compounds comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, or SEQ ID NO:14, or a pharmaceutical acceptable salt thereof, or pharmaceutical compositions comprising the same for use in therapy. The present application further provides the compounds comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14, or a pharmaceutical acceptable salt thereof, or pharmaceutical compositions comprising the same for use in the treatment of diabetes, obesity, dyslipidemia, and/or NASH. The present application also provides the compound comprising SEQ ID NO:2 or a pharmaceutical acceptable salt thereof, or pharmaceutical compositions comprising the same for use in therapy, the treatment of diabetes, obesity, dyslipidemia, and/or NASH. More preferably, the present application provides the compound comprising SEQ ID NO:2 or a pharmaceutical acceptable salt thereof, or pharmaceutical compositions comprising the same for use in the treatment of diabetes. Alternatively, the present application provides the compound comprising SEQ ID NO:2 or a pharmaceutical acceptable salt thereof, or pharmaceutical compositions comprising the same for use in the treatment of obesity. Alternatively, the present application provides the compound comprising SEQ ID NO:2 or a pharmaceutical acceptable salt thereof, or pharmaceutical compositions comprising the same for use in the treatment of dyslipidemia. Alternatively, the present application provides the compound comprising SEQ ID NO:2 or a pharmaceutical acceptable salt thereof, or pharmaceutical compositions comprising the same for use in the treatment of NASH.

The present application provides the compounds comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, or SEQ ID NO:14 or a pharmaceutical acceptable salt thereof, or compositions comprising the same for use in lowering food intake, lowering body weight, lowering blood glucose, lowering HbA1c, and/or lowering triglycerides. More preferably, the present application provides the compounds comprising SEQ ID NO:2 or a pharmaceutical acceptable salt thereof, or compositions comprising the same for use in lowering food intake, lowering body weight, lowering blood glucose, lowering HbA1c, and/or lowering triglycerides.

The present disclosure further provides the use of a compound comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14 or a pharmaceutical acceptable salt thereof, in the manufacture of a medicament for the treatment of diabetes, obesity, dyslipidemia, and/or NASH. Preferably, the present disclosure further provides the use of a compound comprising SEQ ID NO:2 in the manufacture of a medicament for the treatment of diabetes, obesity, dyslipidemia, and/or NASH.

The present disclosure further provides the use of a compound comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14 or a pharmaceutical acceptable salt thereof, in the manufacture of a medicament lowering food intake, lowering body weight, lowering blood glucose, lowering HbA1c, and/or lowering triglycerides. Preferably, the present disclosure further provides the use of a compound comprising SEQ ID NO:2 or a pharmaceutical acceptable salt thereof, in the manufacture of a medicament lowering food intake, lowering body weight, lowering blood glucose, lowering HbA1c, and/or lowering triglycerides.

Unless defined otherwise, all technical and scientific terms used herein have the same meaning as commonly understood by one of skill in the art to which the disclosure pertains. Although any methods and materials similar to or equivalent to those described herein can be used in the practice or testing of the amylin agonist peptides, pharmaceutical compositions and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as, for example, a stated concentration, length, molecular weight, pH, sequence similarity, time frame, temperature, volume, etc. Such a value or range can be within an order of magnitude typically within 20%, more typically within 10%, and even more typically within 5% of a given value or range. The allowable variation encompassed by "about" will depend upon the particular system under study, and can be readily appreciated by one of skill in the art.

As used herein, and in reference to one or more receptors, "activity," "activate," "activating" and the like means a capacity of a compound, such as a peptide herein, to bind to and induce a response at the receptor(s), as measured using assays known in the art, such as the in vitro assays described below.

As used herein the term "amino acid" means both naturally occurring amino acids and non-coded amino acids. As known in the art, an amino acid is a molecule that, from a chemical standpoint, is characterized by presence of one or more amine groups and one or more carboxylic acid groups and may contain other functional groups. Further, amino acids are typically depicted using standard one letters codes (e.g., L=leucine), as well as alpha-methyl substituted residues of natural amino acids (e.g., α-methyl leucine, or αMeL, and α-methyl phenylalanine, or αMeF) and certain other non-coded amino acids, such as "γE", "NMeN", "NMeD", "Orn" and the like. The structures of the non-coded amino acids of the present disclosure appear below:

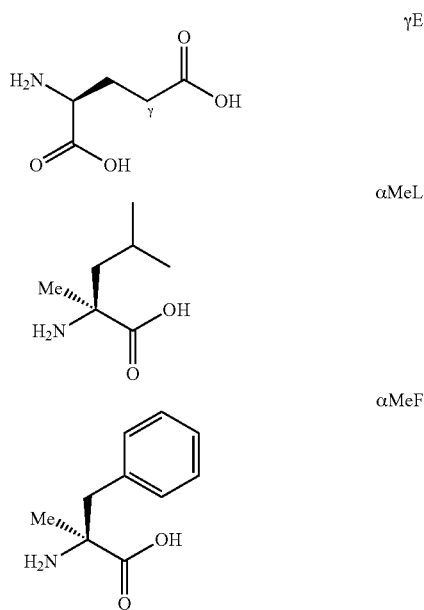

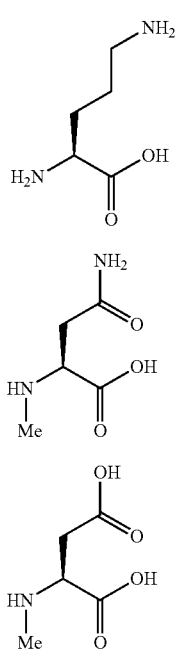

Orn

NMeN

NMeD

As used herein, "γE" means gamma-glutamic acid (where the peptide bond is formed using the side chain carboxylic acid group at the gamma position rather than the typical alpha position). As used herein, "Orn" means L-ornithine. As used herein, "αMeL" means alpha-methyl-L-leucine. As used herein, "αMeF" means alpha-methyl-L-phenylalanine. As used herein, "NMeN" means N-methyl-asparagine and "NMeD" means N-methyl-aspartic acid.

As used herein, "AEEA" means 2-[2-(2-amino-ethoxy)-ethoxy]acetic acid. The structure appears below:

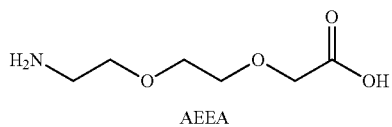 [SMILES: NCCOCCOCC(=O)O]

AEEA

As used herein, "amylin agonist peptide" means a compound, such as a synthetic peptide or polypeptide, that activates a target receptor and that elicits at least one in vivo or in vitro effect elicited by a native agonist for that receptor.

As used herein, "chronic weight management" means a method by which one maintains weight loss as an adjunct to reduced calorie diet and increased physical activity in persons who are currently or have been previously characterized as having obesity.

The term "diabetes" refers to a disease in which the body's ability to produce or respond to the hormone insulin is impaired, resulting in abnormal metabolism of carbohydrates and elevated levels of glucose in the blood and urine. As used herein, the term diabetes may refer to a chronic condition that affects the way the body processes blood sugar, or glucose, e.g., type 2 diabetes mellitus (T2DM); a chronic condition in which the pancreas produces little or no insulin, e.g., type 1 diabetes mellitus (T1DM); a condition in which blood sugar is high, but not high enough to be type 2 diabetes, e.g., pre-diabetes; a form of high blood sugar affecting pregnant women, e.g., gestational diabetes.

The term "dyslipidemia" refers to a disorder of lipoprotein metabolism, including lipoprotein overproduction or deficiency. Dyslipidemias may be manifested by elevation of the total cholesterol, low-density lipoprotein (LDL) cholesterol and triglyceride concentrations, and/or a decrease in the high-density lipoprotein (HDL) concentration in the blood. Dyslipidemia may or may not develop in connection with diabetes.

As used herein, "fatty acid" consists of a straight chain of an even number of carbon atoms, with hydrogen atoms along the length of the chain and at one end (monoacid) or both ends (diacid) of the chain a carboxyl group (—COOH). In a preferred embodiment, the "fatty acid" moiety is a $C_{20}$ diacid.

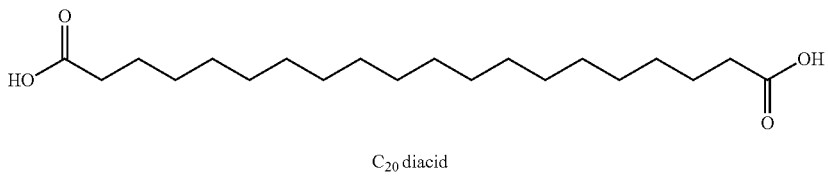 [SMILES: O=C(O)CCCCCCCCCCCCCCCCCCC(=O)O]

$C_{20}$ diacid

As used herein, "thioacetal bridge" refers to an organic synthesis of a thioacetal group to functionally re-bridge disulfide bond[s] within peptide structures. A thioacetal bridge (—S—CH$_2$—S—) is shown below with a methylene group inserted between two sulfur atoms.

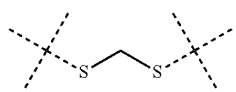

The term "treatment" or "treating" as used herein refers to the management and care of a patient having a condition for which amylin receptor peptide agonist administration is indicated for the purpose of combating or alleviating symptoms and complications of the condition. Treating includes administering a compound or a pharmaceutical composition containing a compound of the presently disclosed compounds to a patient in need thereof to prevent the onset of symptoms or complications, alleviating the symptoms or complications, or eliminating the disease, condition, or disorder. Preferably treating includes administering a compound or pharmaceutical composition containing a compound of the present disclosure to a patient in need thereof to result in a net loss of body weight, a reduction in food intake, a reduction in blood glucose levels, a reduction in HbA1c, and/or a reduction in triglyceride levels. The patient to be treated is a mammal, and preferably a human being.

As used herein, the term "effective amount" means an amount or dose of one or more of the compounds herein, upon a single or multiple dose administration to an individual in need thereof, which provides a desired effect in such an individual under diagnosis or treatment (i.e, may produce a clinically measurable difference in a condition of the individual such as, for example, a net loss of body weight, a reduction in food intake, a reduction in blood glucose levels, a reduction in HbA1c, and/or a reduction in triglyceride levels.). An effective amount can be readily demonstrated by one of skill in the art by using known techniques and by observing results obtained under analogous circumstances. In determining the effective amount for an individual, a number of factors are considered, including, but not limited to, the species of the mammal, its size, age, and general health, the specific disease or disorder involved, the degree of involvement or the severity of the disease or disorder, the response of the individual, the particular compound administered, the mode of administration, the bioavailability characteristics of the preparation administered, the dose regiment selected, the use of concomitant medication, and other relevant circumstances. Preferably an effective amount of a compound or pharmaceutical composition containing a compound of the present disclosure administered to a patient in need thereof would result in a net loss of body weight, a reduction in food intake, a reduction in blood glucose levels, a reduction in HbA1c, and/or a reduction in triglyceride levels. A dose can include a higher initial loading dose, followed by a lower dose. An effective dose of the compounds provided herein may be between 0.05 µg/kg and 5000 µg/kg or 0.01 nmol/kg to 1000 nmol/kg.

As used herein, "half-life" or "$t_{1/2}$" means a time it takes for one-half of a quantity of a compound, such as peptide herein, to be removed from a fluid or other physiological space such as serum or plasma of an individual by biological processes. Alternatively, $t_{1/2}$ can also mean the time it takes for a quantity of such a peptide to lose one-half of its pharmacological, physiological, or radiological activity.

As used herein, "half-maximal effective concentration" or "$EC_{50}$" means a concentration of compound that results in 50% activation/stimulation of an assay endpoint, such as a dose-response curve.

As used herein, "long-acting" means that binding affinity and activity of a composition herein continues for a period of time greater than native peptide or protein, allowing for dosing at least as infrequently as once daily or even thrice-weekly, twice-weekly, once-weekly, or monthly. The time action profile of the compounds herein may be measured using known pharmacokinetic test methods such as those described in the Examples below.

The term "NASH" refers to nonalcoholic steatohepatitis, aka fatty liver disease. "NASH" also refers to liver inflammation and damage caused by a buildup of fat in the liver. "NASH" also refers to a subtype of nonalcoholic fatty liver disease ("NAFLD"). In some embodiments, "NASH" may be synonymous with "NAFLD."

The term "obesity" as used herein refers to a disorder involving excess body fat that increases the risk of health problems. The term "obesity" also refers to weight that is higher than what is considered a healthy weight for a given height. The term "obesity" also refers to a BMI greater than 30.0 or a BMI of 27.0 or greater (overweight) with at least one weight-related comorbid condition (e.g., hypertension, type 2 diabetes mellitus, or dyslipidemia).

As used herein, body mass index (BMI) refers to a person's weight in kilograms divided by the square of height in meters.

As used herein, "patient," and "individual" are used interchangeably, and mean a mammal, and preferably a human being. In certain embodiments, the patient, preferably a human, is further characterized with a disease, disorder or condition that would benefit from administration of a compound that agonizes both the amylin and calcitonin receptors.

In some embodiments, pharmaceutical compositions comprising a presently disclosed compound may be administered orally to patients in need of such treatment. Pharmaceutical compositions comprising a presently disclosed compound may be administered parenterally to patients in need of such treatment. Parenteral administration may be performed by subcutaneous, intramuscular or intravenous injection by means of a syringe, optionally a pen-like syringe, or mechanical driven injector. Alternatively, parenteral administration can be performed by means of an infusion pump. Embodiments of the presently disclosed compounds provide pharmaceutical compositions suitable for administration to a patient comprising administering to a patient in need thereof a therapeutically effective amount of a compound presently disclosed and one or more pharmaceutically acceptable excipients. Such pharmaceutical compositions may be prepared by any of a variety of techniques using conventional excipients for pharmaceutical products which are well known in the art. (Remington's Pharmaceutical Sciences, 21st Edition, University of the Sciences in Philadelphia, Philadelphia, PA, USA (2006)).

As used herein, "sequence similarity" means a quantitative property of two or more nucleic acid sequences or amino acid sequences of biological compounds such as, for example, a correspondence over an entire length or a comparison window of the two or more sequences. Sequence similarity can be measured by (1) percent identity or (2) percent similarity. Percent identity measures a percentage of residues identical between two biological compounds divided by the length of the shortest sequence, whereas percent similarity measures identities and, in addition, includes sequence gaps and residue similarity in the evaluation. Methods of and algorithms for determining sequence similarity are well known in the art and thus need not be exhaustively described herein. A specified percentage of identical nucleotide or amino acid positions is at least about 75%, 80%, 85%, 86, 76, 88, 89, 90, 91, 92, 93, 94, 95, 96, 97, 98, 99% or higher.

The compounds presently disclosed may be used in simultaneous, separate, or sequential combination with one or more additional therapeutic agents useful for inducing weight loss, treating diabetes, conditions related to diabetes, obesity and/or chronic weight management, dyslipidemia, and/or NASH. Non-limiting examples of the additional therapeutic agents that can be combined with the claimed compounds include: insulin or insulin analogs; biguanides; sulfonylureas; thiazolidinediones; dipeptidyl peptidase-4 ("DPP-4") inhibitors; sodium-dependent glucose transporter (SGLT2) inhibitors; incretin compounds such as glucagon-like-peptide-1 (GLP-1) or GLP-1 analogs, gastric inhibitory polypeptide (GIP) or GIP analogs, oxyntomodulin or oxyntomodulin analogs; growth differentiation factor-15 (GDF15) agonist compounds; peptide YY (PYY) analogs; dual GIP/GLP-1 agonists; Gcg/GIP/GLP-1 triagonists (tri-agonists of glucagon, GIP, and GLP-1); or combinations of any of the foregoing agents. The claimed compounds and the additional therapeutic agent(s) can be co-administered through the same delivery route and device such as a single pill, capsule, tablet, or injectable formulation; or separately administered either at the same time in separate delivery devices or routes; or administered sequentially.

Another embodiment of the present disclosure is a method of treating a condition in patient in need thereof, selected from the group consisting of: diabetes, obesity, NASH, and/or dyslipidemia, comprising administering to the patient an effective amount of a compound comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14, or a pharmaceutically acceptable salt thereof, in combination with an effective amount of an incretin or incretin analog. Preferably, an embodiment of the present disclosure is a method of treating a condition in patient in need thereof, selected from the group consisting of: diabetes, obesity, NASH, and/or dyslipidemia, comprising administering to the patient an effective amount of a compound comprising SEQ ID NO:2, or a pharmaceutically acceptable salt thereof, in combination with an effective amount of an incretin or incretin analog.

In a particular embodiment of the present disclosure is a method of treating a condition in patient in need thereof, selected from a group consisting of: diabetes, obesity, NASH, and/or dyslipidemia, comprising administering to a patient in need of such treatment an effective amount of a compound comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14, or a pharmaceutically acceptable salt thereof, in combination with a GLP-1 agonist. In a particular embodiment of the present disclosure is a method of treating a patient with diabetes, obesity, NASH, and/or dyslipidemia, comprising administering to a patient in need of such treatment an effective amount of a compound comprising SEQ ID NO: 1, or a pharmaceutically acceptable salt thereof, in combination with a GLP-1 agonist comprising Compound XVII (SEQ ID NO:18). In another particular embodiment of the present disclosure is a method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with a GLP-1 agonist comprising Compound XVII (SEQ ID NO:18).

In a particular embodiment of the present disclosure is a method of treating a patient with diabetes, obesity, NASH, and/or dyslipidemia, comprising administering to a patient in need of such treatment an effective amount of a compound comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, or SEQ ID NO:14, or a pharmaceutically acceptable salt thereof, in combination with an analog of oxyntomodulin. In a particular embodiment of the present disclosure is a method of treating a patient with diabetes, obesity, NASH, and/or dyslipidemia, comprising administering to a patient in need of such treatment an effective amount of a compound comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14, or a pharmaceutically acceptable salt thereof, in combination with an analog of oxyntomodulin comprising Compound XVIII (SEQ ID NO:19). In another particular embodiment of the present disclosure is a method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with an analog of oxyntomodulin comprising Compound XVIII (SEQ ID NO:19).

In a particular embodiment of the present disclosure is a method of treating a patient with diabetes, obesity, NASH, and/or dyslipidemia, comprising administering to a patient in need of such treatment an effective amount of a compound comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, or SEQ ID NO:14, or a pharmaceutically acceptable salt thereof, in combination with a triagonist of glucagon, GIP, and GLP-1. In a particular embodiment of the present disclosure is a method of treating a patient with diabetes, obesity, NASH, and/or dyslipidemia, comprising administering to a patient in need of such treatment an effective amount of a compound comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO: 9, SEQ ID NO:10, SEQ ID NO:11, SEQ ID NO:12, SEQ ID NO:13, or SEQ ID NO:14, or a pharmaceutically acceptable salt thereof, in combination with a triagonist of glucagon, GIP, and GLP-1 comprising Compound XIX (SEQ ID NO:20). In another particular embodiment of the present disclosure is a method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with a triagonist of glucagon, GIP, and GLP-1 comprising Compound XIX (SEQ ID NO:20).

In a particular embodiment of the present disclosure is a method of treating a patient with diabetes, obesity, NASH, and/or dyslipidemia, comprising administering to a patient in need of such treatment an effective amount of a compound comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14, or a pharmaceutically acceptable salt thereof, in combination with a dual GIP/GLP-1 agonist. In a particular embodiment of the present disclosure is a method of treating a patient with diabetes, obesity, NASH, and/or dyslipidemia, comprising administering to a patient in need of such treatment an effective amount of a compound comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14, or a pharmaceutically acceptable salt thereof, in combination with a dual GIP/GLP-1 agonist comprising SEQ ID NO:21. In another particular embodiment of the present disclosure is a method of treating a patient with diabetes, obesity, NASH, and/or dyslipidemia, comprising administering to a patient in need of such treatment an effective amount of a compound comprising SEQ ID NO:2, or a pharmaceutically acceptable salt thereof, in combination with a dual GIP/GLP-1 agonist comprising SEQ ID NO:21.

Another embodiment of the present disclosure is the compound comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14, or a pharmaceutically acceptable salt thereof, for use in a separate, simultaneous, or sequential combination with an incretin or incretin analog for the treatment of diabetes, obesity, NASH, and/or dyslipidemia. Preferably, an embodiment of the present disclosure is the compound comprising SEQ ID NO:2, or a pharmaceutically acceptable salt thereof, for use in a separate, simultaneous, or sequential combination with an incretin or incretin analog for the treatment of diabetes, obesity, NASH, and/or dyslipidemia. More preferably, the incretin or incretin analog is a dual GIP/GLP-1 agonist comprising SEQ ID NO:21.

Certain abbreviations used herein are defined as follows: "ACN" refers to acetonitrile; "AMY1R" refers to amylin receptor 1; "cAMP" refers to cyclic adenosine monophosphate; "CT" refers to calcitonin; "DCM" refers to dichloromethane; "DIEA" refers to diisopropylethylamine; "DMF" refers to N,N-dimethylformamide; "DMSO" refers to dimethyl sulfoxide; "DODT" refers to 2,2'-(ethylenedioxy)diethanethiol; "FBS" refers to fetal bovine serum; "Fmoc" refers to fluorenylmethyloxycarbonyl; "GDF15" refers to growth differentiation factor 15; "GPCR" refers to G-protein coupled receptor(s); "HEPES" refers to 4-(2-hydroxyethyl)-1-piperazineethanesulfonic acid; "HTRF" refers to homogeneous time resolved fluorescence; "IBMX" refers to 1-methyl-3-isobutylxanthine; "MEM" refers to minimum essential medium; "Mtt" refers to 4-methyltrityl; "NASH" refers to nonalcoholic fatty liver disease; "NEAA" refers to non-essential amino acid; "PyAOP" refers to (7-azabenzotriazol-1-yloxy)tripyrrolidinophosphonium hexafluorophosphate; "RP-HPLC" refers to reverse phase high pressure liquid chromatography; "TCEP" refers to tris(2-carboxyethyl)phosphinehydrochloride"; "TFA" refers to trifluoroacetic acid; and "TRIS" refers to tris(hydroxymethyl)aminomethane.

Example 1: Preparation and Purification of Compounds I and II

Compound I and Compound II are made according to the following steps. First, Compound I (SEQ ID NO:1) is synthesized using Fluorenylmethyloxycarbonyl (Fmoc)/tert-Butyl (t-Bu) chemistry on a Symphony 12-channel multiplex peptide synthesizer (Protein Technologies, Inc. Tucson, AZ).

Polystyrene Rink Amide MBHA resin LL resin (Novabiochem, sub: 0.35 meq/g, 100-200 mesh, Cat #855045) is used for the synthesis at 0.13 mmol scale. Standard side-chain protecting groups are used. Boc-Glu-OtBu is used for position 1. Fmoc-Lys(Mtt)-OH is used for the lysine at position 26. Fmoc groups are removed prior to each coupling step (2×7 minutes) using 20% piperidine in DMF. All amino acid couplings are performed for 30 minutes at 60° C. using an equal molar ratio of Fmoc amino acid (0.3M), diisopropylcarbodiimide (0.9M) and Oxyma (0.9M), at a 7.7-fold molar excess over the theoretical peptide loading. The amino acid couplings following αMeF at position 15 and NMeN at position 22 are performed for 3 h and 6 h respectively at 60° C. For Compound I (SEQ ID NO:1), the resin is treated with cleavage cocktail at this time (conditions described after the procedures for addition of the fatty acid-linker moiety to generate Compound II). Below is a schematic of Compound I (SEQ ID NO:1) using the standard single letter amino acid codes with the exception of the glutamic acid (γE) at position 1 (where the peptide bond is formed using its side chain carboxylic acid group at the gamma position rather than the typical alpha position), the cysteines at positions 2 and 7, Orn at position 11, αMeF at position 15, NMeN at position 22, and tyrosine at position 37, where the structures of these amino acid residues have been expanded:

Then, the resin is thoroughly washed with DCM 6 times to remove residual DMF. The Mtt protecting group on the lysine at position 26 is selectively removed from the peptide resin using two treatments of 30% hexafluoroisopropanol (Oakwood Chemical) in DCM (2×40-minute treatment). Subsequent attachment of the fatty acid-linker moiety is accomplished by coupling Fmoc-glutamic acid α-t-butyl ester (Fmoc-Glu-OtBu, Ark Pharm, Inc.), mono-OtBu-eicosanoic acid (WuXi AppTec, Shanghai, China). 3-Fold excess of reagents (AA: PyAOP: DIEA=1: 1:1 mol/mol) are used for each 1-hour long coupling.

After the synthesis is complete, the peptide resin is washed with DCM, and then thoroughly air-dried. The dry resin is treated with 10 mL of cleavage cocktail (TFA: DODT: TIS: $H_2O$=89:3:3:5 v/v) for 2 hours at room temperature. The resin is filtered off, washed twice each with 2 mL of neat TFA, and the combined filtrates are treated with 4-fold cold diethyl ether (−20° C.) to precipitate the crude peptide. The peptide/ether suspension is then centrifuged at 3500 rpm for 2 min to form a solid pellet, the supernatant is decanted, and the solid pellet is triturated with ether two additional times. To make the thioacetal bridge, the pellet after air drying is dissolved in 5 mL of 20 mM potassium phosphate buffer and 3 mL of ACN. Once completely dissolved, under good stirring, TCEP in $H_2O$ (30 μM, 5 eq), diiodomethane (8 eq) and triethylamine (10 eq) are added and left to stir for 5-30 mins. LCMS is used to monitor the reaction, which usually completes in 5 mins. After the reaction is complete, 1 mL of $H_2O$ w/0.1% TFA is added to the mixture as well as 6 mL of acetic acid. More ACN is added as needed if the solution is cloudy.

The crude peptide is purified by RP-HPLC on a Phenomenex PhenylHexyl column (5 μm, 100 A, 250×21.2 mm, Part Number:00G-4257-P0-AX) with a linear gradient using a 100% acetonitrile and 0.1% TFA/water buffer system. The purity of the peptide is assessed using analytical RP-HPLC using a Waters SymmetryShield RP18 column (3.5 um, 6×100 mm, Part 186000179) and pooling criteria is >95%. The main pool purity of Compound II (SEQ ID NO:2) is found to be >98.4%. Subsequent lyophilization of the final main product pool yields the lyophilized peptide TFA salt. The molecular weight of Compound I (SEQ ID NO:1) is determined by LC/MS (Found: $[M+3H]^{3+}$=1315.2; Calc. $[M+3H]^{3+}$=1315.5; Found MW (avg)=3942.6; Calc. MW (avg)=3943.4). The molecular weight of Compound II (SEQ ID NO: 2) is determined by LC/MS (Found: $[M+3H]^{3+}$=1509.5; Calc. $[M+3H]^{3+}$=1509.7; Found MW (avg) =4525.5; Calc. MW (avg)=4526.1). Below is a schematic of Compound II (SEQ ID NO:2) using the standard single letter amino acid codes with the exception of the glutamic acid (γE) at position 1 (where the peptide bond is formed using its side chain carboxylic acid at the gamma position rather than the typical alpha position), the cysteines at position 2 and 7, Orn at position 11, αMeF at position 15, NMeN at position 22, lysine at position 26, and tyrosine at position 37 where the structures of these amino acid residues have been expanded:

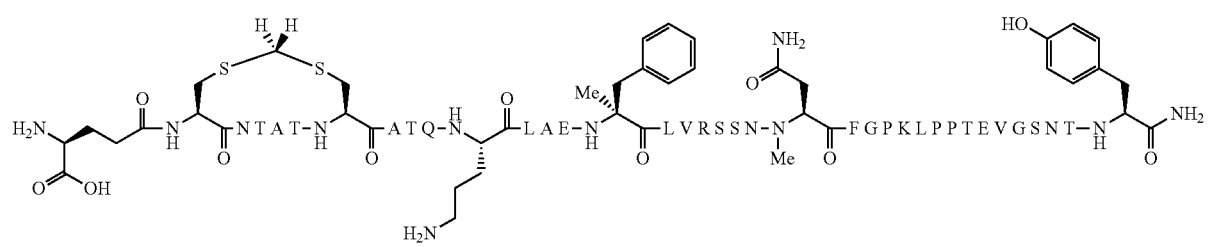

Compound I; SEQ ID NO: 1

Compound II; SEQ ID NO: 2

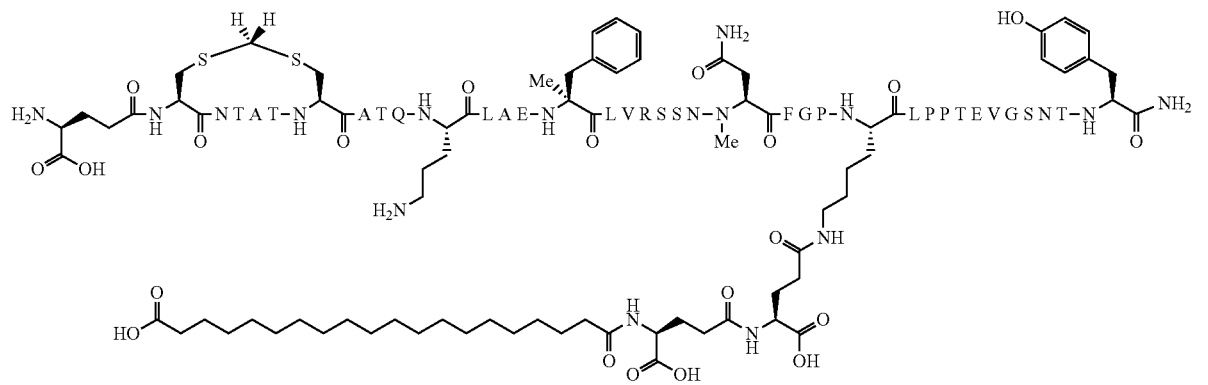

Similar processes to those described above and known to those of skill in the art may be used to synthesize the peptide backbone, conjugate the fatty acid-linker moiety, examine the purity, and confirm the molecular weight of the inventive compounds described herein.

Example 2: Preparation and Purification of Compounds III and IV

Compounds III and IV are made according to the processes outlined in Example 1.

Below is a schematic of Compound III (SEQ ID NO:3) using the standard single letter amino acid codes with the exception of the glutamic acid (γE) at position 1 (wherein the peptide bond is formed using its side chain carboxylic acid group at the gamma position rather than the typical alpha position), the cysteines at positions 2 and 7, Orn at position 11, αMeF at position 15, NMeD at position 22, and tyrosine at position 37 where the structures of these amino acid residues have been expanded:

Compound III; SEQ ID NO: 3

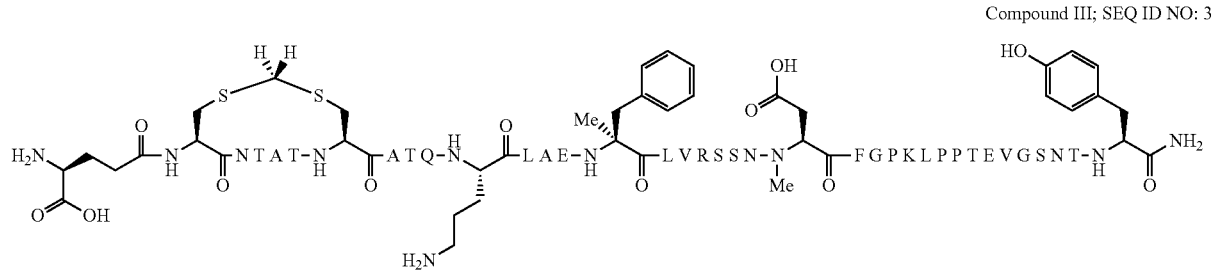

The molecular weight of Compound III (SEQ ID NO:3) is determined by LC/MS (Found: $[M+3H]^{3+}$=1314.9; Calc. $[M+3H]^{3+}$=1315.8; Found MW (avg)=3941.7; Calc. MW (avg)=3944.4).

Below is a schematic of Compound IV (SEQ ID NO:4) using the standard single letter amino acid codes with the exception of the glutamic acid (γE) at position 1 (where the peptide bond is formed using its side chain carboxylic acid group at the gamma position rather than the typical alpha position), the cysteines at positions 2 and 7, Orn at position 11, αMeF at position 15, NMeD at position 22, lysine at position 26, and tyrosine at position 37 where the structures of these amino acid residues have been expanded:

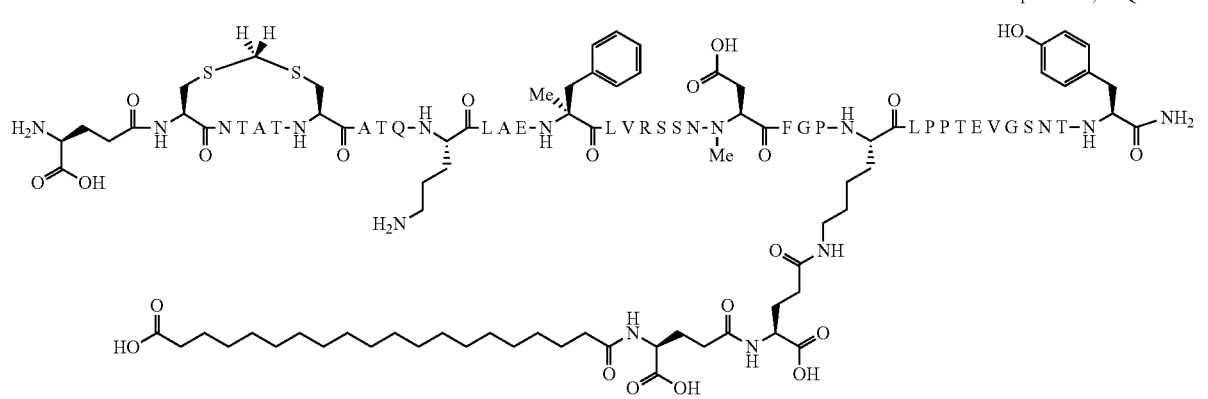

Compound IV; SEQ ID NO: 4

The molecular weight is determined by LC/MS (Found: $[M+3H]^{3+}=1509.7$; Calc. $[M+3H]^{3+}=1510.0$; Found MW (avg)=4526.1; Calc. MW (avg)=4527.1).

Example 3: Preparation and Purification of Compound V and VI

Compounds V and VI are made according to the processes outlined in Example 1.

Below is a schematic of Compound V (SEQ ID NO:5) using the standard single letter amino acid codes with the exception of cysteines at positions 2 and 7, Orn at position 11, αMeF at position 15, NMeD at position 22, and tyrosine at position 37 where the structures of these amino acid residues have been expanded:

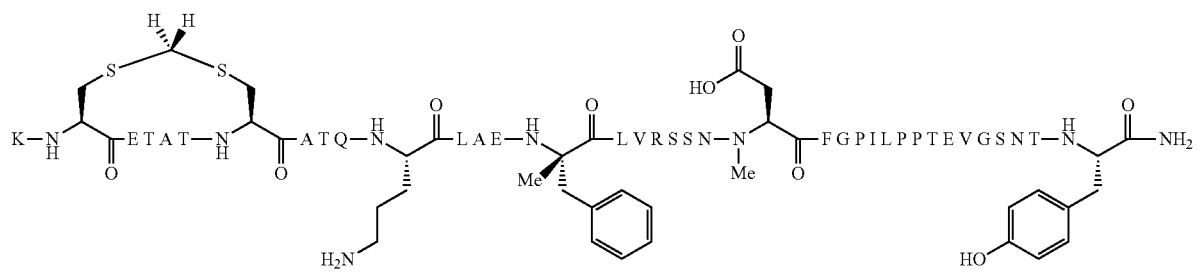

Compound V; SEQ ID NO: 5

The molecular weight of Compound V (SEQ ID NO:5) is determined by LC/MS (Found: $[M+3H]^{3+}=1314.9$; Calc. $[M+3H]^{3+}=1315.5$; Found MW (avg)=3941.7; Calc. MW (avg)=3943.4).

Below is a schematic of Compound VI (SEQ ID NO:6) using the standard single letter amino acid codes with the exception of the lysine at position 1, the cysteines at positions 2 and 7, Orn at position 11, αMeF at position 15, NMeD at position 22, and tyrosine at position 37 where the structures of these amino acid residues have been expanded:

Compound VI; SEQ ID NO: 6

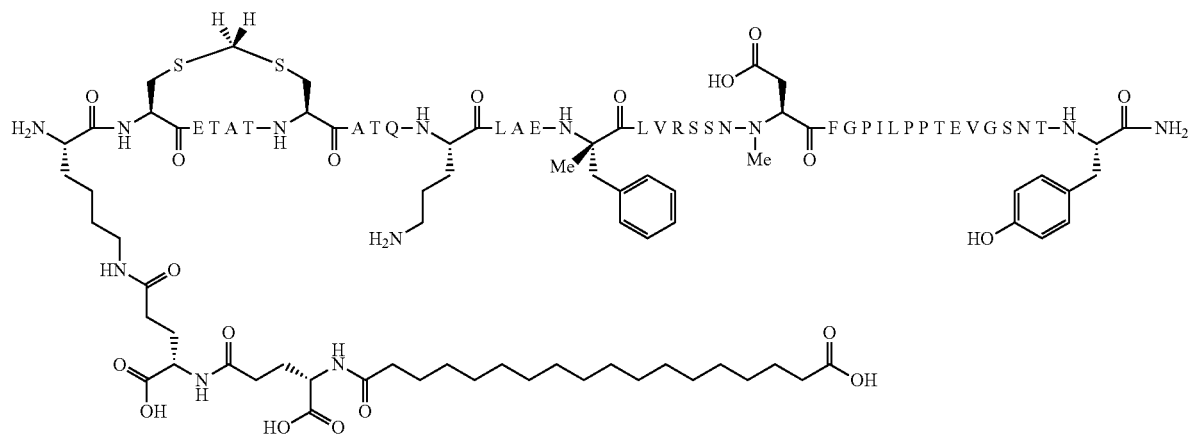

The molecular weight is determined by LC/MS (Found: $[M+3H]^{3+}$=1509.4; Calc. $[M+3H]^{3+}$=1509.7; Found MW (avg)=4525.2; Calc. MW (avg)=4526.1).

Example 4: Preparation and Purification of Compound VII and VIII

Compounds VII and VIII are made according to the processes outlined in Example 1.

Below is a schematic of Compound VII (SEQ ID NO:7) using the standard single letter amino acid codes with the exception of the cysteines at positions 2 and 7, Orn at position 11, αMeL at position 12, and tyrosine at position 37 where the structures of these amino acid residues have been expanded:

Compound VII; SEQ ID NO: 7

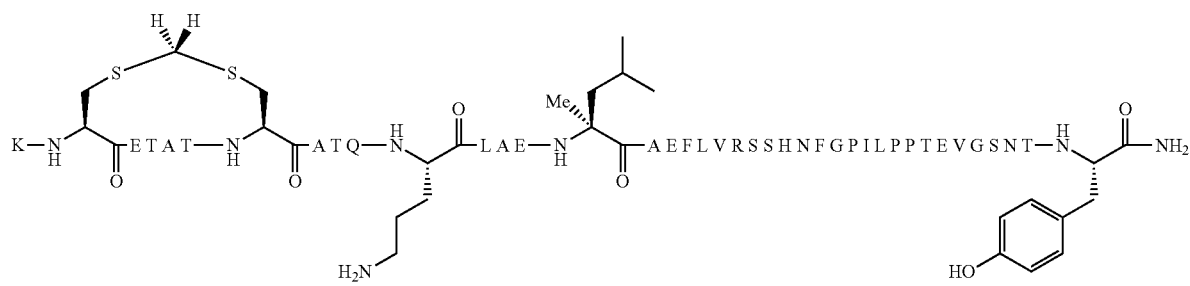

The molecular weight of Compound VII (SEQ ID NO:7) is determined by LC/MS (Found: $[M+3H]^{3+}$=1317.9; Calc. $[M+3H]^{3+}$=1318.1; Found MW (avg)=3950.7; Calc. MW (avg)=3951.4).

Below is a schematic of Compound VIII (SEQ ID NO:8) using the standard single letter amino acid codes with the exception of the lysine at position 1, the cysteines at positions 2 and 7, Orn at position 11, αMeL at position 12, and tyrosine at position 37 where the structures of these amino acid residues have been expanded:

Compound VIII; SEQ ID NO: 8

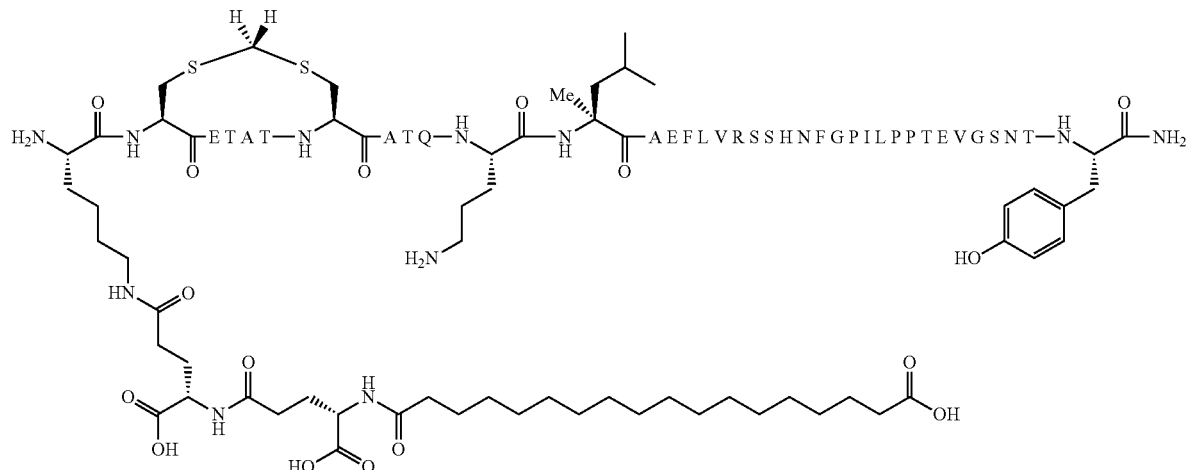

The molecular weight is determined by LC/MS (Found: $[M+3H]^{3+}=1512.2$; Calc. $[M+3H]^{3+}=1512.4$; Found MW (avg)=4533.6; Calc. MW (avg)=4534.2).

Example 5: Preparation and Purification of Compound IX

Compound IX is made according to the processes outlined in Example 1.

Below is a schematic of Compound IX (SEQ ID NO:9) using the standard single letter amino acid codes with the exception of the glutamic acid (γE) at position 1 (where the peptide bond is formed using its side chain carboxylic acid group at the gamma position rather than the typical alpha position), the cysteines at positions 2 and 7, lysine at position 26, and tyrosine at position 37 where the structures of these amino acid residues have been expanded:

Compound IX; SEQ ID NO: 9

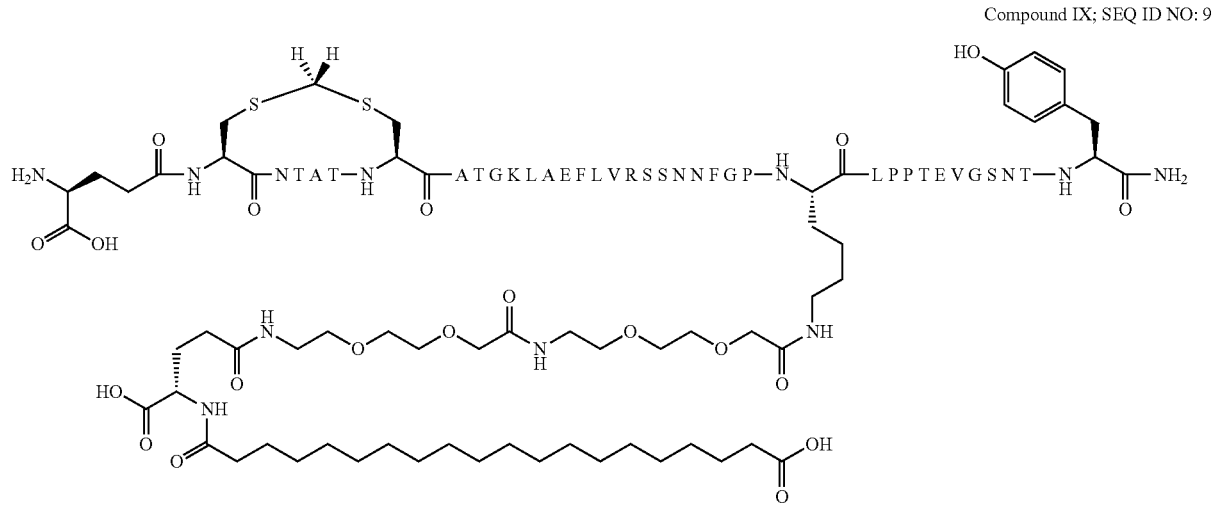

The molecular weight is determined by LC/MS (Found: $[M+H]^{3+}=1558.3$; Calc. $[M+3]^{3+}=1558.8$; Found MW (avg)= 4671.9; Calc. MW (avg)=4673.3).

Example 6: Preparation and Purification of Compound X

Compound X is made according to the processes outlined in Example 1.

Below is a schematic of Compound X (SEQ ID NO:10) using the standard single letter amino acid codes with the exception of the glutamic acid (γE) at position 1 (where the peptide bond is formed using its side chain carboxylic acid group at the gamma position rather than the typical alpha position), the cysteines at positions 2 and 7, lysine at position 26, and tyrosine at position 37 where the structures of these amino acid residues have been expanded:

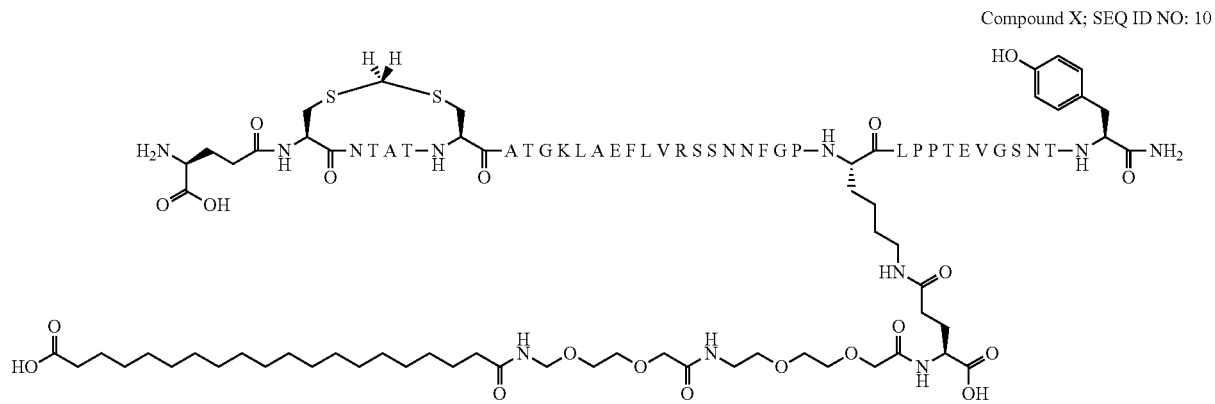

Compound X; SEQ ID NO: 10

The molecular weight is determined by LC/MS (Found: $[M+3H]^{3+}=1558.5$; Calc. $[M+3H]^{3+}=1558.8$; Found MW (avg)=4672.5; Calc. MW (avg)=4673.3).

Example 7: Preparation and Purification of Compound XI

Compound XI is made according to the processes outlined in Example 1.

Below is a schematic of Compound XI (SEQ ID NO:11) using the standard single letter amino acid codes with the exception of the glutamic acid (γE) at position 1 (where the peptide bond is formed using its side chain carboxylic acid group at the gamma position rather than the typical alpha position), the cysteines at positions 2 and 7, lysine at position 26, and tyrosine at position 37 where the structures of these amino acid residues have been expanded:

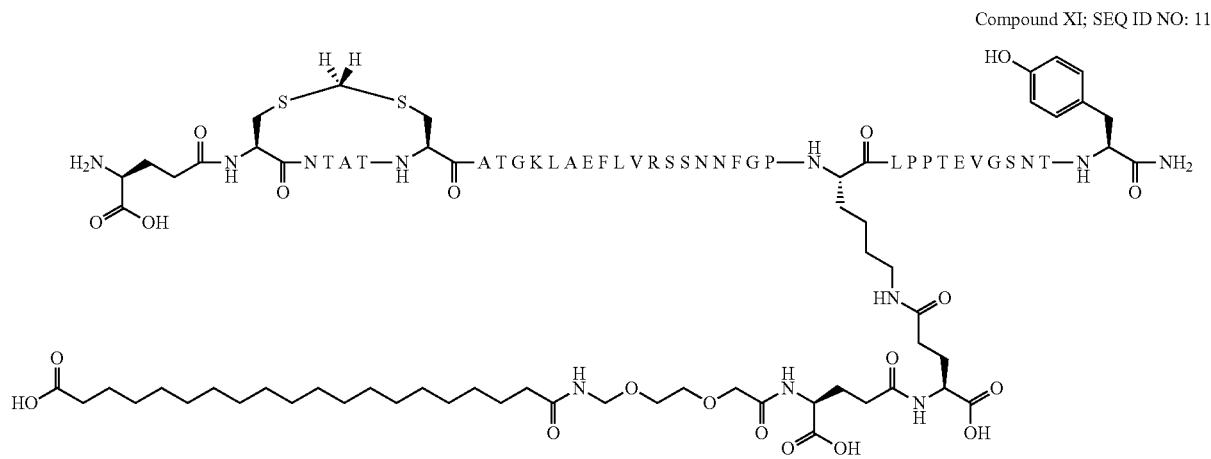

Compound XI; SEQ ID NO: 11

The molecular weight is determined by LC/MS (Found: $[M+3H]^{3+}=1553.2$; Calc. $[M+3H]^{3+}=1553.4$; Found MW (avg)=4656.6; Calc. MW (avg)=4657.2).

Example 8: Preparation and Purification of Compound XII

Compound XII is made according to the processes outlined in Example 1.

Below is a schematic of Compound XII (SEQ ID NO:12) using the standard single letter amino acid codes with the exception of the glutamic acid (γE) at position 1 (where the peptide bond is formed using its side chain carboxylic acid group at the gamma position rather than the typical alpha position), the cysteines at positions 2 and 7, Orn at position 11, lysine at position 26, and tyrosine at position 37 where the structures of these amino acid residues have been expanded:

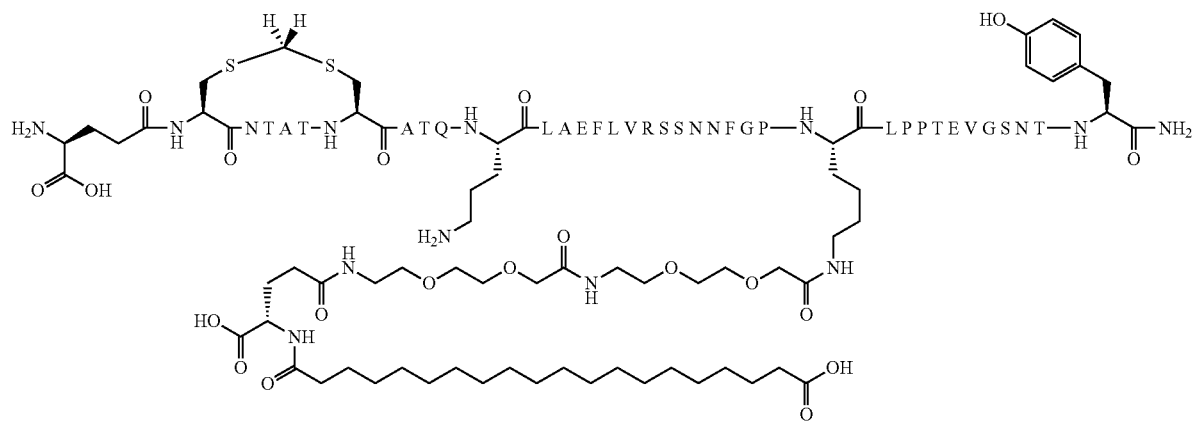

Compound XII; SEQ ID NO: 12

The molecular weight is determined by LC/MS (Found: $[M+3H]^{3+}=1577.4$; Calc. $[M+3H]^{3+}=1577.8$; Found MW (avg)=4729.2; Calc. MW (avg)=4730.3).

Example 9: Preparation and Purification of Compound XIII

Compound XIII is made according to the processes outlined in Example 1.

Below is a schematic of Compound XIII (SEQ ID NO:13) using the standard single letter amino acid codes with the exception of the glutamic acid (γE) at position 1 (where the peptide bond is formed using its side chain carboxylic acid group at the gamma position rather than the typical alpha position), the cysteines at positions 2 and 7, Orn at position 11, lysine at position 26, and tyrosine at position 37 where the structures of these amino acid residues have been expanded:

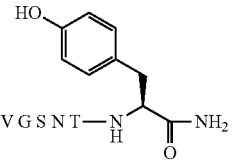

Compoound XIII: SEQ ID NO: 13

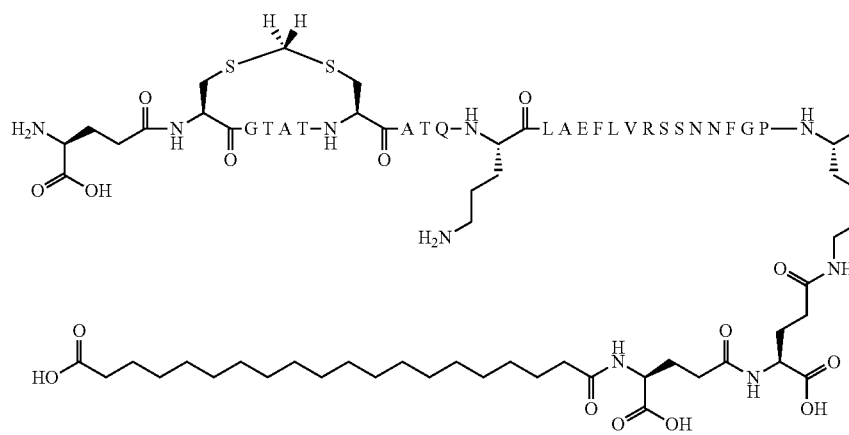

The molecular weight is determined by LC/MS (Found: [M+3H]$^{3+}$=1481.2; Calc. [M+3H]$^{3+}$=1481.3; Found MW (avg)=1440.6; Calc. MW (avg)=4441.0).

Disulfide Bond Bridge Preparation

To make the disulfide bond, the oxidation solution is prepared by adding 10 drops of Iodine solution (2% Iodine in AcOH) to 40 mL of 20% MeCN/20% AcOH/60% water in a flask. Separately, a peptide solution is made by dissolving the peptide pellet after air drying in 5 ml of AcOH. Under stirring, the peptide solution is added dropwise to the oxidation solution. Additional iodine solution (2% Iodine in AcOH) is added as needed to maintain a light yellow solution in the flask. The light brown/yellow color is maintained for 5 min after all the peptide solution is added. Extra iodine is neutralized by adding one drop of saturated ascorbic acid to the oxidation solution. The solution is filtered with a 0.45 μm filter and the peptide is ready for purification.

Example 10: In Vitro Functional Activity of Amylin Agonist Peptides

The AMY1 and CT receptors are GPCRs that are functionally coupled to Gas proteins. Stimulation of these receptors results in an increased production of intracellular cAMP, which can be detected using standard in vitro technologies. In vitro activity of peptides is measured by the amount of cAMP formed in human AMY1R and CTR overexpressed cells.

Human CT receptors are stably expressed in human urinary bladder cells (UM-UC-3, or UMUC3) under control of a pcDNA expression vector. The UMUC3 cell line is cultured in MEM 1X (Meditech Inc., 17-305-CV) supplemented with 10% FBS, 1% antibiotic/antimycotic solution, 1 mM sodium pyruvate, 1X MEM NEAA, 1X GlutaMAX-I. The plasmid of human CTa-pcDNA3.1Hygro(+)(T2616) DNA is transfected into UMUC3 cells using LipofectAMINE 2000 Transfection reagent (Invitrogen, 11668-019). After 20 days under selection, the mRNA levels from different clones are measured to confirm the expression of hCTR. To determine the function of over-expressed hCTR cells, the intracellular cAMP levels in response to salmon calcitonin are measured and compared to the expression of hCTR mRNA in each clone.

Human AMY1R stable cell lines are generated by further transfecting human RAMP1-pCMVpuroPB (T14213) into UMUC3 hCTR clone cells. After selection, the mRNA levels human RAMP1 from different clones are measured to confirm the expression of human AMY1R.

hAMY1R cells are cultured in MEM 1X (Corning) supplemented with 10% FBS, 1% antibiotic/antimycotic solution, 1 mM sodium pyruvate, 1X MEM NEAA, 1X GlutaMAX-I, 200 μg/mL hygromycin B, and 0.4 μg/mL puromycin. The hCTR cells are cultured in the same medium lacking the puromycin. Cultured cells are grown to 70% confluency and then incubated overnight with fresh medium.

On the day of the assay, 10 μL of assay buffer (phenol red free MEM (Corning, cat #17-305-CV), 0.1% casein, 0.5 mM IBMX, 5 mM HEPES, pH 7.4) is dispensed into each well of white poly-D-lysine coated 384-well plates (Corning cat #354661). Peptides diluted in DMSO are added (200 nL/well) in a 1:3 dilution series using ECHO acoustic liquid handler (Beckman). Cultured cells are detached with TrypLE Express (Gibco), resuspended in assay buffer, and 10 μL containing 1200 cells/well (hCTR) or 1500 cells/well (hAMY1R) are dispensed into each well. The plates are incubated at room temperature for 1 hour.

The amount of intracellular cAMP is quantitated using HTRF technology (Homogeneous Time Resolved Fluorescence; Cisbio) as per vendor instructions. Briefly, 10 μL cAMP-d2 conjugate and 10 μL anti-cAMP-cryptate conjugate in lysis buffer are incubated with the treated cells at room temperature for 60 min. The HTRF signal is immediately detected using an Envision plate reader (Perkin-Elmer) to calculate the ratio of fluorescence at 665 to 620 nm. The raw data are converted to cAMP amount (pmol/well) using a cAMP standard curve generated for each experiment. Relative EC$_{50}$ values are calculated from the top-bottom range of the concentration response curve defined using 1 nM salmon CT (Bachem) as the maximum and buffer alone as the minimum with a four-parameter logistic curve fitting program (Genedata Screener® v12.0.4). The compounds of the present application show selective activity at the amylin receptor versus the calcitonin receptor as shown in Table 1.

TABLE 1

Comparison of Functional Activity Data at
Amylin and Calcitonin Receptors

| Compound Number | hAMY1R cAMP EC50 (pM, ± SE) | hCTR cAMP EC50 (pM, ±SE) |
|---|---|---|
| I | 133 ± 12 | 18000 ± 1080 |
| II | 75 ± 12 | 2340 ± 272 |
| III | 156 ± 27 | 16300 ± 3030 |
| IV | 107 ± 16 | 6140 ± 764 |
| V | 139 ± 17 | 17000 ± 2440 |
| VI | 107 ± 15 | 13200 ± 2230 |
| VII | 173 ± 34 | 11900 ± 1530 |
| VIII | 107 ± 20 | 9690 ± 2010 |
| IX | 132 ± 20 | 18900 ± 3830 |
| X | 80 ± 13 | 14000 ± 3320 |
| XI | 38 ± 7.8 | 10500 ± 2200 |
| XII | 113 ± 34 | 25900 ± 7620 |
| XIII | 78 ± 14 | 9490 ± 1540 |
| XV | 43 ± 4.4 | 2400 ± 402 |
| XVI | 393 ± 51 | 103 ± 20 |

Example 11: In Vitro Binding Affinity of Amylin Agonist Peptides to hAMY1 and hCT Receptors The membranes from human AMY1R and CTR overexpressed cells (described in Example 10) were isolated via a standard method and used for the binding assays. The equilibrium dissociation constants (Kd) for the various receptor/radioligand interactions are determined from saturation binding analysis using the same reagents and buffers as described below for compound testing. The Kd values determined for the receptor preparations used in this study are as follows: hAMY1R, 0.067 nM; human calcitonin receptor (hCTR), 0.046 nM.

hAMY1R Binding Protocol

The receptor binding affinity (Ki) of rAMY, hCT, and hAMY agonist peptides are determined from a competitive radioligand binding filter assay. The assay buffer consists of (in mM) 50 HEPES, pH 7.1, 5 $MgCl_2$, 5 KCl, 0.2% (w/v) bacitracin, 0.003% (w/v) saponin and is used to dilute radioligand and membrane preparation. Binding reactions are carried out in 0.1 mL total reaction volume in a polystyrene 96 deep-well assay block. Iodinated rat amylin (ViTrax custom synthesis; 2200 Ci/mmol; 125I-rAMY) is initially diluted to approximately 50 pM in assay buffer. Test compounds and non-specific binding (NSB—defined as 300 nM rAMY) are added to aliquots of radioactivity buffer. Briefly, test compounds are diluted to 200 nM initial concentration, serially diluted in 4-fold steps in 125I-rAMY, and then 0.05 ml of diluted test compound, NSB, or total binding (defined as neat 125I-rAMY) are transferred to the 96 well polystyrene assay block. The binding reaction is initiated by the addition of 0.05 mL of 200 µg/mL hAMY1R diluted in assay buffer to the radioactivity. Assay blocks are gently vortexed, sealed with parafilm, and incubated at RT for approximately 20 hours. Thirty minutes before the incubation is complete, filter mats (Perkin Elmer printed filter mats Cat #1450-421) are soaked in a solution consisting of assay buffer minus saponin but supplemented with 0.1% (w/v) fatty-acid free bovine serum albumin (FAF-BSA) and 0.5% (v/v) polyethyleneimine (PEI). At the end of the incubation, bound ligand is separated from free by addition of an ice cold quench buffer consisting of 100 mM NaCl, 50 mM TRIS-HCl pH 7.1 and immediately collected over the filter mat by vacuum filtration with a TomTec 96 well filter harvester using the following filter protocol (Dry time, 7; Cycle 3 repeat, 0; Wash Time, 1; Soak Time, 1; 1st Aspirate Time, 4; Wash/Aspirate Time, 7; 2nd Aspirate, 4; air pressure 2 PSI). Final assay concentration range for peptides tested in response curves is 100 nM-0.00038 nM.

hCTR Binding Protocol

The receptor binding affinity (Ki) of rAMY, hCT, and hAMY agonist peptides on hCTR membranes is determined from a competitive radioligand binding filter assay. The assay procedures are similar to that of hAMY1R binding assay, except 125I-hCT (ViTrax custom synthesis; 2200 Ci/mmol) is used as the hot ligand. Binding reactions are carried out in 0.2 mL total reaction volume with 14 pM 125I-hCT and 20 µg/ml hCTR membrane and incubated for 20 hours. Final assay concentration range for peptides tested in response curves is 2500 nM-0.00128 nM. The compounds of the present application show selective activity at the amylin receptor versus the calcitonin receptor as shown in Table 2.

TABLE 2

In vitro Binding (Ki) at Human Amylin and Calcitonin Receptors

| Compound Number | hAMY1R, Ki (nM ± SE) | hCTR, Ki (nM ± SE) |
|---|---|---|
| II | 0.017 ± 0.006 | 202 ± 45 |
| IV | 0.0296 ± 0.0099 | 665 ± 113 |
| VI | 0.0445 ± 0.0082 | 235 ± 45 |
| VIII | 0.0435 ± 0.0072 | 927 ± 120 |
| XV | 0.0196 ± 0.0020 | 0.256 ± 0.087 |
| XVI | 0.701 ± 0.148 | 0.104 ± 0.043 |

Example 12: In Vivo Effects on Food Intake and Body Weights in Normal Rats

Male Sprague Dawley rats from Envigo RMS (Indianapolis, IN) are maintained on a chow diet (2014; Teklad Global, Envigo RMS, Indianapolis, IN) and single housed in a temperature-controlled facility (72.0° F.; 22.2° C.) with a reversed 12:12-hour light cycle (10 AM OFF) and free access to food and water. At 10 weeks of age, non-fasted body weights and initial food weights are recorded, and animals are administered a single subcutaneous injection (SC) of vehicle or acylated peptide (1 mL/kg), followed by daily measurements of body weight and food intake for 4 days post dose. Area under the curve analysis (AUC) is calculated for both body weight and food intake versus vehicle.

TABLE 3

Changes in Body Weight and Food Intake for 4 Days in Sprague Dawley Rats Following a Single Dose of Long-Acting Amylin Agonist Peptide

| Compound Number | Dose (nmol/kg, SC) | Δ Body Weight (%)* | Cumulative Food Intake Inhibition (%)** |
|---|---|---|---|
| II | 0.1 | 1.8 | −4.1 |
| | 0.3 | 2.4 | −3.7 |
| | 1 | 0.5 | −18.6 |
| | 3 | −3.3 | −37.9 |
| | 10 | −7.4 | −57.3 |
| | 30 | −10.1 | −69.8 |
| | 100 | −12.9 | −77.9 |
| | 300 | −14.9 | −84.5 |
| | 1000 | −17.2 | −87.1 |
| IV | 0.1 | 1.4 | −1.1 |
| | 0.3 | 1.8 | −2.0 |
| | 1 | 0.8 | −5.6 |
| | 3 | −2.0 | −20.5 |

TABLE 3-continued

Changes in Body Weight and Food Intake for 4 Days in Sprague Dawley Rats Following a Single Dose of Long-Acting Amylin Agonist Peptide

| Compound Number | Dose (nmol/kg, SC) | Δ Body Weight (%)* | Cumulative Food Intake Inhibition (%)** |
|---|---|---|---|
|  | 10 | −5.2 | −46.8 |
|  | 30 | −9.2 | −59.2 |
|  | 100 | −11.9 | −68.1 |
|  | 300 | −14.2 | −79.2 |
|  | 1000 | −16.4 | −82.9 |
| VI | 0.1 | 2.2 | 2.3 |
|  | 0.3 | 1.2 | −0.4 |
|  | 1 | 1.2 | −0.4 |
|  | 3 | −0.9 | −23.8 |
|  | 10 | −3.6 | −36.4 |
|  | 30 | −8.3 | −58.9 |
|  | 100 | −12.7 | −73.4 |
|  | 300 | −14.1 | −76.9 |
|  | 1000 | −16.2 | −84.6 |
| VIII | 0.1 | 2.0 | 1.3 |
|  | 0.3 | 1.6 | 3.2 |
|  | 1 | −1.0 | −17.5 |
|  | 3 | −3.9 | −37.7 |
|  | 10 | −7.2 | −58.5 |
|  | 30 | −10.8 | −67.0 |
|  | 100 | −13.8 | −75.2 |
|  | 300 | −13.6 | −74.9 |
|  | 1000 | −18.9 | −84.7 |

*Change in average body weights at 96 hours post dose compared to initial weights of naïve animals.
**Cumulative food intake of peptide-treated animals at 96 hours post dose versus vehicle treated animals at 96 hours post dose.

Example 13: In Vivo Effects on Food Intake and Body Weights in Diet-Induced Obese Rats Male Long Evan rats from Envigo RMS (Indianapolis, IN) at 14 weeks of age are put on a high fat diet (40% of kcal from fat, TD.95217; Envigo RMS, Indianapolis, IN) until 35-45 weeks old. Animals are individually housed in a temperature-controlled facility (75.0° F.; 23.9° C.) with a 12-hour reverse light/dark cycle (lights OFF at 10 AM) and free access to food and water. Body weights are recorded and body composition (fat mass) is determined using Quantitative Nuclear Magnetic Resonance Analysis (ECHO MRI, 3-1 Composition Analyzer; Echo Medical Systems, Houston, TX), followed by randomization into experimental groups (n=5). Rats are administered subcutaneous injections of vehicle or peptide (1 mL/kg) every three days (day 1, 4, 7, 10, and 13). Daily body weights are recorded and changes at end of treatment (day 14) are calculated as percentages versus pre-treatment weights (day 1). Body composition is determined on day 14, and changes in fat mass and fat-free mass (body weight—fat mass) are calculated from pre-treatment values as gram changes.

TABLE 4

Changes in Body Weight in a 2-Week Study in Diet-Induced Obese Rats with Amylin Agonist Peptides

| Compound Number | Dose (nmol/kg, SC) | Δ Body Weight (%)* | Δ Fat Mass (g)* | Δ Fat-Free Mass (g)* |
|---|---|---|---|---|
| II | 1 | −7.1 | −43.8 | −7.5 |
|  | 10 | −9.0 | −59.6 | −5.6 |
|  | 100 | −10.7 | −61.0 | −15.4 |
| IV | 1 | −4.5 | −31.0 | −0.2 |
|  | 10 | −8.5 | −53.5 | −6.4 |
|  | 100 | −8.9 | −52.9 | −8.6 |
| VI | 1 | −3.2 | −25.5 | 1.9 |
|  | 10 | −8.8 | −51.9 | −9.1 |
|  | 100 | −9.8 | −54.7 | −15.2 |
| VIII | 1 | −6.0 | −36.6 | −4.7 |
|  | 10 | −9.0 | −54.3 | −7.2 |
|  | 100 | −11.5 | −56.4 | −26.9 |

*Change in average body weights or fat mass or fat-free mass at 2 weeks compared to initial weights of naive animals.

Example 14: Pharmacokinetics in Male Sprague Dawley Rats

The pharmacokinetics of Compound II (SEQ ID NO:2), Compound IV (SEQ ID NO:4), Compound VI (SEQ ID NO:6), and Compound VIII (SEQ ID NO:8) are evaluated following a single subcutaneous administration of 30 nmol/kg to male Sprague Dawley rats. Blood samples are collected at 1, 3, 6, 12, 24, 48, 72, 96 hours post SC dose. The resulting individual plasma concentrations are used to calculate pharmacokinetic parameters. Peptide plasma ($K_3$EDTA) concentrations are determined using a qualified LC/MS method that measured the intact mass of the peptides. Each peptide and an analog as an internal standard are extracted from plasma. A high resolution Thermo Q-Exactive is used for LC/MS detection. Mean pharmacokinetic parameters are shown in Table 5.

TABLE 5

Mean Pharmacokinetic Parameters of peptides Following a Single Subcutaneous Administration of 30 nmol/kg to Male Sprague Dawley Rats.

| Compound Number | $T_{1/2}$ (hr) | $T_{max}$ (hr) | $C_{max}$/D (kg*nmol/L/nmol) | AUCINF/D (hr*kg*nmol/L/nmol) | Cl/F (mL/hr/kg) |
|---|---|---|---|---|---|
| II | 52.8 ± 6.6 | 24.0 ± 0.0 | 4.9 ± 0.9 | 473 ± 63.8 | 2.1 ± 0.3 |
| IV | 66.9 ± 27.6 | 20.0–6.9 | 5.5 ± 2.1 | 551 ± 27.1 | 1.8 ± 0.1 |
| VI | 54.0 ± 8.4 | 24.0–0.0 | 5.4 ± 0.5 | 506 ± 26.6 | 2.0 ± 0.1 |
| VIII | 36.4 ± 2.93 | 16.0–6.9 | 3.8 ± 0.4 | 270 ± 22.4 | 3.7 ± 0.3 |

Abbreviations:
$T_{1/2}$ = half-life,
$T_{max}$ = time to maximal concentration,
$C_{max}$/D = maximal plasma concentration divided by dose,
AUCINF/D = AUCinf divided by dose,
CL/F = clearance/bioavailability.
Notes:
Data are the mean, where n = 3/group.

Example 15: Pharmacokinetics in Male Cynomolgus Monkeys

The pharmacokinetics of Compound II (SEQ ID NO:2), Compound IV (SEQ ID NO:4), Compound VI (SEQ ID NO:6), and Compound VIII (SEQ ID NO:8) are evaluated following a single subcutaneous administration of 20 nmol/kg to male cynomolgus monkeys. Blood samples are collected at 1, 3, 6, 12, 24, 48, 72, 120, 168, 240, 336, 408, 504 hours post SC dose. The resulting individual plasma concentrations are used to calculate pharmacokinetic parameters. Peptide plasma ($K_3$EDTA) concentrations are determined using a qualified LC/MS method that measured the intact mass of the peptides. Each peptide and an analog as an internal standard are extracted from plasma. A high resolution Thermo Q-Exactive is used for LC/MS detection. Mean pharmacokinetic parameters are shown in Table 6.

TABLE 6

Mean Pharmacokinetic Parameters of peptides Following a Single Subcutaneous Administration of 20 nmol/kg to Cynomolgus Monkeys.

| Compound Number | $T_{1/2}$ (hr) | $T_{max}$ (hr) | $C_{max}$/D (kg*nmol/L/nmol) | AUCINF/D (hr*kg*nmol/L/nmol) | Cl/F (mL/hr/kg) |
|---|---|---|---|---|---|
| II | 159 ± 7.7 | 64.0 ± 13.9 | 6.7 ± 1.0 | 1752 ± 313 | 0.58 ± 0.1 |
| IV | 177 ± 13.5 | 48.0 ± 24.0 | 6.2 ± 1.0 | 1607 ± 104 | 0.62 ± 0.04 |
| VI | 85.0 ± 5.8 | 40.0 ± 13.9 | 4.9 ± 0.7 | 794 ± 27 | 1.26 ± 0.04 |
| VIII | 62.0 ± 4.7 | 28.0–18.3 | 7.2 ± 0.3 | 942 ± 67 | 1.07 ± 0.1 |

Abbreviations:
$T_{1/2}$ = half-life,
$T_{max}$ = time to maximal concentration,
$C_{max}$/D = maximal plasma concentration divided by dose,
AUCINF/D = AUCinf divided by dose,
CL/F = clearance/bioavailability.
Notes:
Data are the mean, where n = 3/group.

Example 16: Immunogenicity Risk Assessment

Dendritic Cell (DC) Internalization Assay

This assay assesses the ability of human DCs to internalize tested antibodies. CD14+ cells are cultured and differentiated into immature DCs with IL-4 and GM-CSF. Tested antibodies, isotype control, or a positive control are pre-incubated with the detection agent (Fab-QSY7-TAMRA) in a 1:1 ratio to form a complex and then added to the cultures. Cells are incubated for one day. Upon internalization and cleavage, a positive TAMRA signal is detected by flow cytometry, and a normalized internalization index is calculated using IgG1-EN isotype control and anti-CXCR antibody.

MAPPS Assay (MHC-Associated Peptide Proteomics)

MAPPS profiles the MHC-II presented peptides on human dendritic cells treated with tested molecules. CD14+ cells, isolated from the PBMCs of normal human donors, are cultured and differentiated into immature DCs by incubation with IL-4 and GM-CSF. On day 4, culture media is replaced with fresh media containing tested molecules. On day 5, LPS is added to transform the cells into mature DCs. On day 6, cells are lysed in RIPA buffer with protease inhibitors. Immunoprecipitation of MHC-II complexes are performed using biotinylated anti-MHC-II antibody coupled to streptavidin beads. The bound complex is eluted and filtered. The isolated MHC-II peptides are analyzed by a mass spectrometer. Peptide identifications are generated by an internal proteomics pipeline using search algorithms with no enzyme and a bovine/human database with test sequences appended to the database. A KNIME workflow is used to process the identification files from the samples. Peptides identified from the test articles are aligned against the parent sequence of the test molecule. The output is used to determine the percentage of donors displaying MHC-II peptides from regions of the test molecule. Compound II, Compound IV, Compound VI, Compound VIII, a compound representative of U.S. Pat. No. 9,023,789 (hereinafter "Compound '789"), and Pramlintide are tested in the MAPPs assay. Compound II, Compound IV, Compound VI, Compound VIII show no peptides displayed on MHC-II complexes in the assay. Compound '789 displays a peptide cluster spanning residues 8-23 on MHC-II complexes. Pramlintide shows two peptide clusters that in total span residues 1-34 that are displayed on MHC-II complexes.

In-Silico TCEM (T-Cell Exposed Motif) Analysis

This analysis assesses the likelihood that specific peptide clusters, identified by MAPPS, will activate CD4+ T cells. MAPPS-identified peptide sequences containing non-germline residues are inputted into an ImmunoEpitope Database (IEDB) Analysis Resource MHCII binding prediction page. The IEDB-recommended prediction method is selected. The prediction considers the 27 most frequent HLA-DR, -DP and -DQ alleles to cover a significant fraction of human population. Each input sequence, with a length equal or greater than 15 residues, is divided into overlapping 15-mers offset 1 amino acid to span the entire sequence. For each peptide, a percentile rank is generated by comparing the peptide's score against the scores of five million random 15 mers selected from SWISSPROT database. Amino acids located at the putative P-1, P2, P3, P5, P7, and P8 positions of the register generate the TCEM, and risk is defined on the basis of presence of non-germline residues at these positions. Non-germline residues and likelihood of the core binding to multiple alleles are reported in a graphic rendering and considered for immunogenicity risk assessment.

MS Serum Binding

This assay assesses off-target binding of a test candidate to human serum proteins. Tested antibodies are coated onto an Immulon 4 HBX microplate. Following blocking, human serum is added and incubated overnight. The plate is washed, and bound proteins are eluted, reduced, alkylated, and digested. The peptides are analyzed by a mass spectrometer. Peptide identifications are generated by an internal proteomics pipeline using search algorithms with tryptic enzyme specificity and a human database with the test molecule sequences appended. Ions are quantified by internal proteomics tools (Chrom-Alignment, Metaconsense and Quant) and analyzed in JMP using Oneway analysis/Each Pair, Student's t test platform. Analysis on log 2auc for ions using JMP: Fit Y by X per each ion/Compare Means/All pairs, Tukey HSD.

sion of the Tier 1 signal. The presence of pre-existing anti-drug antibodies is expressed as magnitude of the $90^{th}$ percentile of Tier 2 inhibition. The $90^{th}$ percentile of Tier 2 inhibition, is a statistical tool to assess the magnitude of specificity of Tier 1 reactivity. This $90^{th}$ percentile is used to rank molecules in terms of ADA risk.

TABLE 7

Immunogenicity Risk Assessment Summary

| Assay | Pramlintide | Compound '789 | Compound II | Compound IV | Compound VI | Compound VIII |
|---|---|---|---|---|---|---|
| MAPPS Assay 10 donors with diverse MHC | High Risk 10/10 donors displayed peptides | High Risk 5/10 donors displayed peptides | Low Risk no peptides displayed | Low Risk no peptides displayed | Low Risk no peptides displayed | Low Risk no peptides displayed |
| T Cell Proliferation Assay: protein 7-10 donors with diverse MHC | High Risk (7/7 positive donors) | Low Risk (1/7 positive donors) | Low Risk (0/9 positive donors) | Low Risk (0/9 positive donors) | Low Risk (1/9 positive donors) | Low Risk (1/9 positive donors) |
| Pre-existing Reactivity $90^{th}$ percentile T2 inhibition >50 donors | N/A | 58.0% | 48.8% | 33.2% | 43.9% | 51.4% |

Abbreviations:
ACE = acid capture elution;
ADA = anti-drug antibodies;
CDR = complementarity determining region;
DC = dendritic cell;
H1 = VH CDR1;
H2 = VH CDR2;
H3 = VH CDR3;
L1 = VL CDR1;
L2 = VL CDR2;
MAPPs = MHC-associated peptide proteomics;
MHC = major histocompatibility complex;
MS = mass spectrometry;
T2 = Tier 2;
TCEM = T cell exposed motif;
VH = variable heavy;
VL = variable light;
VHFR3 = variable heavy framework 3

T Cell Proliferation Assay

This assay assesses the ability of tested antibodies or tested MAPPS peptides to activate CD4+ T cells by inducing cellular proliferation. CD8+ T cell depleted PBMC's are prepared and labeled with CFSE. Each sample is tested with media control, keyhole limpet haemocyanin (KLH; positive clinical benchmark control), tested antibodies, or tested MAPPS peptides. Cultures are incubated for 7 days. On day 7, samples are analyzed by flow cytometry.

Pre-Existing Reactivity (ACE AssayFormat)

This assay assesses the presence of pre-existing antibodies (ADA) against the tested molecules in treatment-naive normal human serum (NHS). Diluted NHS is incubated overnight on a Pierce Streptavidin plate coated with biotinylated tested molecules. On the following day, the captured binding proteins are acid eluted, hard-coated to a Mesoscale (MSD) plate, and detected with a combination of biotin-labeled molecule and ruthenium-labeled streptavidin. If anti-drug antibodies are present, they will bind the labeled drug and the resulting signal is referred to as Tier 1 signal (expressed as electrochemiluminescence). This signal is confirmed in Tier 2 by adding excess unlabeled tested molecule in the detection step, which results in the suppres- Example 17: In Vivo Efficacy in Diet Induced Obese (DIO) Rats of Compound II in Combination with Other Incretin Compounds This study is conducted to investigate the effect of Compound II for diabetes and/or obesity conditions in DIO rats when administered in combination with other incretin compounds, including a GLP-1 agonist (Compound XVII), oxyntomodulin analog (Compound XVIII), and a triagonist of glucagon, GLP-1, and GIP (Compound XIX). Diet-induced obese (DIO) male Long Evans (Envigo) rats, maintained on a calorie rich diet since arrival at Lilly (TD95217; Teklad, Madison, WI), are used in the following studies. Animals are individually housed in a temperature-controlled (24° C.) facility with 12-hour light/dark cycle (lights on 2200) and free access to food (TD95217) and water.

The rats are randomized according to their body weight, so that each experimental group of animals would have similar body weight. The body weights range from 529 to 823 grams.

Each group contains five rats. Vehicle and Compound II (1 nmol/kg) are dissolved in vehicle (20 mM Tris-HCl pH8+0.02% PS80) and are administered by subcutaneous (SC) injection (1 mL/kg) to ad libitum fed DIO rats 30 to 90 minutes prior to the onset of the dark cycle every 3 days for 14 days. SC injections are made on Days 1, 4, 7, 10 and 13. Body weight and food intake are measured daily throughout the study. Absolute changes in body weight are calculated by subtracting the body weight of the same animal prior to the first injection of molecule.

At the end of the study, blood is collected to measure blood glucose and plasma insulin. Blood glucose is measured by AccuChek glucometers (Roche, Indianapolis, IN). Insulin is measured by ELISA (MSD, Rockville, MD).

All data are presented as mean ±SEM of 5 animals per group. Statistical analysis is performed using one-way ANOVA, followed by Tukey's multiple comparison test to compare treatment groups to vehicle group or each other. Significant differences are identified at p<0.05.

TABLE 8

The effect of Compound II With and Without Combinations with Compound XVII, Compound XVIII or Compound XIX on Body Weight and Cumulative Food Intake.

| Treatment* | Body Weight Change (g)** | Cumulative Food Intake (g)*** |
|---|---|---|
| Vehicle (10 ml/kg) | −3.42 ± 6.10 | 212.08 ± 16.84 |
| Compound II (1 nmol/kg) | −35.90 ± 3.95* | 149.94 ± 10.88* |
| Compound XVII (10 nmol/kg) | −54.20 ± 6.52* | 150.04 ± 5.71* |
| Compound XVIII (10 nmol/kg) | −50.24 ± 6.36* | 165.86 ± 7.45* |
| Compound XIX (3 nmol/kg) | −43.28 ± 2.54* | 157.50 ± 10.63* |
| Compound II + Compound XVII | −80.68 ± 6.44*# | 98.60 ± 16.46* |
| Compound II + Compound XVIII | −59.96 ± 6.87*# | 137.78 ± 14.66* |
| Compound II + Compound XIX | −63.22 ± 10.11*# | 118.84 ± 11.99* |

*Treatments were subcutaneously administered every three days on Day 1, 4, 7, 10 and 13.
**Body weight measurements were made daily. Body weight change is the difference from Day-1 to Day 14 represented as grams.
***Cumulative food intake was the total food consumed throughout 14-day treatment period. Statistical analysis was done by one-way ANOVA followed by Tukey's.
*p < 0.05 compared to vehicle group;
p < 0.05 compared to either Compound XVII, Compound XVIII or Compound XIX group;
$p < 0.05 compared to Compound II.

There is greater weight loss for the combination of Compound II with Compound XVII, Compound XVIII or Compound XIX than with Compound II alone.

Sequences

SEQ ID NO: 1: Compound I
γE-CNTATCATG-Orn-LAE-αMeF-LVRSSN-NMeN-

FGPKLPPTEVGSNTY-NH$_2$ wherein there is a thioacetal bridge between the cysteines at positions 2 and 7

SEQ ID NO: 2: Compound II
γE-CNTATCATG-Orn-LAE-αMeF-LVRSSN-NMeN-

FGPKLPPTEVGSNTY-NH$_2$ wherein there is a thioacetal bridge between the cysteines at positions 2 and 7 wherein the lysine at position 26 is attached to a fatty acid linker moiety according to the formula (γE)$_2$-CO—(CH$_2$)$_{18}$—CO$_2$H SEQ ID NO: 3: Compound III
γE-CNTATCATG-Orn-LAE-αMeF-LVRSSN-NMeD-

FGPKLPPTEVGSNTY-NH$_2$ wherein there is a thioacetal bridge between the cysteines at positions 2 and 7

SEQ ID NO: 4: Compound IV
γE-CNTATCATG-Orn-LAE-αMeF-LVRSSN-NMeD-

FGPKLPPTEVGSNTY-NH$_2$ wherein there is a thioacetal bridge between the cysteines at positions 2 and 7 wherein the lysine at position 26 is attached to a fatty acid linker moiety according to the formula (γE)$_2$-CO—(CH$_2$)$_{18}$—CO$_2$H SEQ ID NO: 5: Compound V
KCETATCATG-Orn-LAE-αMeF-LVRSSN-NMeD-

FGPILPPTEVGSNTY-NH$_2$ wherein there is a thioacetal bridge between the cysteines at positions 2 and 7

SEQ ID NO: 6 Compound VI
KCETATCATG-Orn-LAE-αMeF-LVRSSN-NMeD-

FGPILPPTEVGSNTY-NH$_2$ wherein there is a thioacetal bridge between the cysteines at positions 2 and 7 wherein the lysine at position 1 is attached to a fatty acid linker moiety according to the formula (γE)$_2$-CO—(CH$_2$)$_{18}$—CO$_2$H SEQ ID NO: 7: Compound VII
KCETATCATG-Orn-αMeL-AEFLVRSSHNFGPILPPTEVGSNTY-NH$_2$ wherein there is a thioacetal bridge between the cysteines at positions 2 and 7

SEQ ID NO: 8: Compound VIII
KCETATCATG-Orn-αMeL-AEFLVRSSHNFGPILPPTEVGSNTY-NH$_2$ wherein there is a thioacetal bridge between the cysteines at positions 2 and 7 wherein the lysine at position 1 is attached to a fatty acid linker moiety according to the formula (γE)$_2$-CO—(CH$_2$)$_{18}$—CO$_2$H SEQ ID NO: 9: Compound IX
γE-CNTATCATGKLAEFLVRSSNNFGPKLPPTEVGSNTY-NH$_2$ wherein there is a thioacetal bridge between the cysteines at positions 2 and 7 wherein the lysine at position 26 is attached to a fatty acid linker moiety according to the formula AEEA$_{2-γ}$E-CO—(CH$_2$)$_{18}$—CO$_2$H SEQ ID NO: 10: Compound X
γE-CNTATCATGKLAEFLVRSSNNFGPKLPPTEVGSNTY-NH$_2$ wherein there is a thioacetal bridge between the cysteines at positions 2 and 7 wherein the lysine at position 26 is attached to a fatty acid linker moiety according to the formula γE-AEEA$_2$-CO—(CH$_2$)$_{18}$—CO$_2$H SEQ ID NO: 11: Compound XI
γE-CNTATCATGKLAEFLVRSSNNFGPKLPPTEVGSNTY-NH$_2$ wherein there is a thioacetal bridge between the cysteines at positions 2 and 7 wherein the lysine at position 26 is attached to a fatty acid linker moiety according to the formula (γE)$_2$-AEEA-CO—(CH$_2$)$_{18}$—CO$_2$H SEQ ID NO: 12: Compound XII
γE-CNTATCATQ-Orn-LAEFLVRSSNNFGPKLPPTEVGSNTY-NH$_2$ wherein there is a thioacetal bridge between the cysteines at positions 2 and 7 wherein the lysine at position 26 is attached to a fatty acid linker moiety according to the formula AEEA$_2$-γE-CO—(CH$_2$)$_{18}$—CO$_2$H SEQ ID NO: 13: Compound XIII
γE-CGTATCATG-Orn-LAEFLVRSSNNFGPKLPPTEVGSNTY-NH$_2$ wherein there is a thioacetal bridge between the cysteines at positions 2 and 7 wherein the lysine at position 26 is attached to a fatty acid linker moiety according to the formula γE$_2$-CO—(CH$_2$)$_{18}$—CO$_2$H SEQ ID NO: 14: Compound XIV
Xaa$_1$-C-Xaa$_3$-TATCAT-Xaa$_{10}$-Xaa$_{11}$-Xaa$_{12}$-AE-Xaa$_{15}$-LVRSS-Xaa$_{21}$-Xaa$_{22}$-FGP-Xaa$_{26}$-LPPTEVGSNTY-NH$_2$.

wherein
Xaa$_1$ is K or γE
Xaa$_3$ is E, N, or G
Xaa$_{10}$ is G or Q;
Xaa$_{11}$ is Orn or K;
Xaa$_{12}$ is L or αMeL
Xaa$_{15}$ is αMeF or F
Xaa$_{21}$ is N or H
Xaa$_{22}$ is NMeD, NMeN, or N
Xaa$_{26}$ is I or K SEQ ID NO: 15: Compound XV; Pramlintide
KCNTATCATQRLANFLVHSSNNFGPILPPTNVGSNTY-NH$_2$ Wherein there is a disulfide bridge between the cysteines at positions 2 and 7

SEQ ID NO: 16: Compounds XVI; hCT
CGNLSTCMLGTYTQDFNKFHTFPQTAIGVGAP-NH$_2$

Wherein there is a disulfide bridge between the cysteines at positions 1 and 7

SEQ ID NO: 17: hAMY
KCNTATCATQRLANFLVHSSNNFGAILSSTNVGSNTY-Nth

Wherein there is a disulfide bridge between the cysteines at positions 2 and 7

SEQ ID NO: 18 Compound XVII
H-Aib-EGTFTSDVSSYLEGQAAK((2-[2-(2-Amino-ethoxy)-ethoxy]-acetyl)$_2$-(γGlu)-CO-(CH$_2$)$_{16}$-CO$_2$H)EFIAWLVRGRG SEQ ID NO:19 Compound XVIII
H-Aib-QGTFTSDYSKYLDEKKAK((2-[2-(2-Amino-ethoxy)-ethoxy]-acetyl)$_2$-(γGlu)-CO-(CH$_2$)$_{18}$-CO$_2$H) EFVEWLLEGGPSSG-NH$_2$ SEQ ID NO: 20 Compound XIX
Y-Aib-QGTFTSDYSI-αMeL-LDKK((2-[2-(2-Amino-ethoxy)-ethoxy]-acetyl)-(γGlu)-CO-(CH$_2$)$_{18}$-CO$_2$H)AQ-Aib-AFIEYLLEGGPSSGAPPPS-NH$_2$

SEQ ID NO: 21
YX$_1$EGTFTSDYSIX2LDKIAQKAFVQWLIAGGPSSGAPPPS wherein X$_1$ is Aib; X$_2$ is Aib; K at position 20 is chemically modified through conjugation to the epsilon-amino group of the K side-chain with (2-[2-(2-Amino-ethoxy)-ethoxy]-acetyl)$_2$-(γGlu)$_1$-CO—(CH$_2$)$_{18}$—CO$_2$H; and the C-terminal amino acid is amidated as a C-terminal primary amide.

SEQ ID NO: 22: Compound I Backbone
γE-CNTATCATG-Orn-LAE-αMeF-LVRSSN-NMeN-FGPKLPPTEVGSNTY-NH$_2$ SEQ ID NO: 23: Compound III Backbone
γE-CNTATCATG-Orn-LAE-αMeF-LVRSSN-NMeD-FGPKLPPTEVGSNTY-NH$_2$ SEQ ID NO: 24: Compound V Backbone
KCETATCATG-Orn-LAE-αMeF-LVRSSN-NMeD-FGPILPPTEVGSNTY-NH$_2$ SEQ ID NO: 25: Compound VII Backbone
KCETATCATG-Orn-αMeL-AEFLVRSSHNFGPILPPTEVGSNTY-NH$_2$

---

SEQUENCE LISTING

<160> NUMBER OF SEQ ID NOS: 25

<210> SEQ ID NO 1
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is gamma-Glu
<220> FEATURE:
<221> NAME/KEY: MISC_FEATURE

```
<222> LOCATION: (11)..(11)
<223> OTHER INFORMATION: Xaa at position 11 is Orn
<220> FEATURE:
<221> NAME/KEY: MISC_FEATURE
<222> LOCATION: (15)..(15)
<223> OTHER INFORMATION: Xaa at position 15 is alpha-methyl-Phe
<220> FEATURE:
<221> NAME/KEY: MISC_FEATURE
<222> LOCATION: (22)..(22)
<223> OTHER INFORMATION: Xaa at position 22 is N-methyl-Asn
<220> FEATURE:
<221> NAME/KEY: MOD_RES
<222> LOCATION: (37)..(37)
<223> OTHER INFORMATION: Tyr at position 37 is amidated

<400> SEQUENCE: 1

Xaa Cys Asn Thr Ala Thr Cys Ala Thr Gly Xaa Leu Ala Glu Xaa Leu
1               5                   10                  15

Val Arg Ser Ser Asn Xaa Phe Gly Pro Lys Leu Pro Pro Thr Glu Val
            20                  25                  30

Gly Ser Asn Thr Tyr
            35

<210> SEQ ID NO 2
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is gamma-Glu
<220> FEATURE:
<221> NAME/KEY: MOD_RES
<222> LOCATION: (2)..(7)
<223> OTHER INFORMATION: There is a thioacetal bridge between the
     cysteines at positions 2 and 7
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MISC_FEATURE
<222> LOCATION: (15)..(15)
<223> OTHER INFORMATION: Xaa at position 15 is alpha-methyl-Phe
<220> FEATURE:
<221> NAME/KEY: MISC_FEATURE
<222> LOCATION: (22)..(22)
<223> OTHER INFORMATION: Xaa at position 22 is N-methyl-Asn
<220> FEATURE:
<221> NAME/KEY: MOD_RES
<222> LOCATION: (26)..(26)
<223> OTHER INFORMATION: The lysine at position 26 is attached to a
     fatty acid linker moiety according to the formula
     (gamma-Glu)2-CO-(CH2)18-CO2H
<220> FEATURE:
<221> NAME/KEY: MOD_RES
<222> LOCATION: (37)..(37)
<223> OTHER INFORMATION: Tyr at position 37 is amidated

<400> SEQUENCE: 2

Xaa Cys Asn Thr Ala Thr Cys Ala Thr Gly Xaa Leu Ala Glu Xaa Leu
1               5                   10                  15

Val Arg Ser Ser Asn Xaa Phe Gly Pro Lys Leu Pro Pro Thr Glu Val
            20                  25                  30

Gly Ser Asn Thr Tyr
            35

<210> SEQ ID NO 3
<211> LENGTH: 37
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is gamma-Glu
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MISC_FEATURE
<222> LOCATION: (15)..(15)
<223> OTHER INFORMATION: Xaa at position 15 is alpha-methyl-Phe
<220> FEATURE:
<221> NAME/KEY: MISC_FEATURE
<222> LOCATION: (22)..(22)
<223> OTHER INFORMATION: Xaa at position 22 is N-methyl-Asp
<220> FEATURE:
<221> NAME/KEY: MOD_RES
<222> LOCATION: (37)..(37)
<223> OTHER INFORMATION: Tyr at position 37 is amidated

<400> SEQUENCE: 3

Xaa Cys Asn Thr Ala Thr Cys Ala Thr Gly Xaa Leu Ala Glu Xaa Leu
 1               5                  10                  15

Val Arg Ser Ser Asn Xaa Phe Gly Pro Lys Leu Pro Pro Thr Glu Val
            20                  25                  30

Gly Ser Asn Thr Tyr
        35

<210> SEQ ID NO 4
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is gamma-Glu
<220> FEATURE:
<221> NAME/KEY: MOD_RES
<222> LOCATION: (2)..(7)
<223> OTHER INFORMATION: There is a thioacetal bridge between the
      cysteines at positions 2 and 7
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MISC_FEATURE
<222> LOCATION: (15)..(15)
<223> OTHER INFORMATION: Xaa at position 15 is alpha-methyl-Phe
<220> FEATURE:
<221> NAME/KEY: MISC_FEATURE
<222> LOCATION: (22)..(22)
<223> OTHER INFORMATION: Xaa at position 22 is N-methyl-Asp
<220> FEATURE:
<221> NAME/KEY: MOD_RES
<222> LOCATION: (26)..(26)
<223> OTHER INFORMATION: The lysine at position 26 is attached to a
      fatty acid linker moiety according to the formula
      (gamma-Glu)2-CO-(CH2)18-CO2H
<220> FEATURE:
<221> NAME/KEY: MOD_RES
<222> LOCATION: (37)..(37)
<223> OTHER INFORMATION: Tyr at position 37 is amidated

<400> SEQUENCE: 4

Xaa Cys Asn Thr Ala Thr Cys Ala Thr Gly Xaa Leu Ala Glu Xaa Leu
 1               5                  10                  15
```

```
Val Arg Ser Ser Asn Xaa Phe Gly Pro Lys Leu Pro Pro Thr Glu Val
            20                  25                  30

Gly Ser Asn Thr Tyr
        35

<210> SEQ ID NO 5
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MISC_FEATURE
<222> LOCATION: (15)..(15)
<223> OTHER INFORMATION: Xaa at position 15 is alpha-methyl-Phe
<220> FEATURE:
<221> NAME/KEY: MISC_FEATURE
<222> LOCATION: (22)..(22)
<223> OTHER INFORMATION: Xaa at position 22 is N-methyl-Asp
<220> FEATURE:
<221> NAME/KEY: MOD_RES
<222> LOCATION: (37)..(37)
<223> OTHER INFORMATION: Tyr at position 37 is amidated

<400> SEQUENCE: 5

Lys Cys Glu Thr Ala Thr Cys Ala Thr Gly Xaa Leu Ala Glu Xaa Leu
1               5                   10                  15

Val Arg Ser Ser Asn Xaa Phe Gly Pro Ile Leu Pro Pro Thr Glu Val
            20                  25                  30

Gly Ser Asn Thr Tyr
        35

<210> SEQ ID NO 6
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: The lysine at position 1 is attached to a fatty
      acid linker moiety according to the formula
      (gamma-Glu)2-CO-(CH2)18-CO2H
<220> FEATURE:
<221> NAME/KEY: MOD_RES
<222> LOCATION: (2)..(7)
<223> OTHER INFORMATION: There is a thioacetal bridge between the
      cysteines at positions 2 and 7
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MISC_FEATURE
<222> LOCATION: (15)..(15)
<223> OTHER INFORMATION: Xaa at position 15 is alpha-methyl-Phe
<220> FEATURE:
<221> NAME/KEY: MISC_FEATURE
<222> LOCATION: (22)..(22)
<223> OTHER INFORMATION: Xaa at position 22 is N-methyl-Asp
<220> FEATURE:
<221> NAME/KEY: MOD_RES
<222> LOCATION: (37)..(37)
<223> OTHER INFORMATION: Tyr at position 37 is amidated

<400> SEQUENCE: 6
```

```
Lys Cys Glu Thr Ala Thr Cys Ala Thr Gly Xaa Leu Ala Glu Xaa Leu
1               5                   10                  15

Val Arg Ser Ser Asn Xaa Phe Gly Pro Ile Leu Pro Pro Thr Glu Val
            20                  25                  30

Gly Ser Asn Thr Tyr
            35

<210> SEQ ID NO 7
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MISC_FEATURE
<222> LOCATION: (12)..(12)
<223> OTHER INFORMATION: Xaa at position 12 is alpha-Methyl-Leu
<220> FEATURE:
<221> NAME/KEY: MOD_RES
<222> LOCATION: (37)..(37)
<223> OTHER INFORMATION: Tyr at position 37 is amidated

<400> SEQUENCE: 7

Lys Cys Glu Thr Ala Thr Cys Ala Thr Gly Xaa Xaa Ala Glu Phe Leu
1               5                   10                  15

Val Arg Ser Ser His Asn Phe Gly Pro Ile Leu Pro Pro Thr Glu Val
            20                  25                  30

Gly Ser Asn Thr Tyr
            35

<210> SEQ ID NO 8
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: The lysine at position 1 is attached to a fatty
      acid linker moiety according to the formula
      (gamma-Glu)2-CO-(CH2)18-CO2H
<220> FEATURE:
<221> NAME/KEY: MOD_RES
<222> LOCATION: (2)..(7)
<223> OTHER INFORMATION: There is a thioacetal bridge between the
      cysteines at positions 2 and 7
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MISC_FEATURE
<222> LOCATION: (12)..(12)
<223> OTHER INFORMATION: Xaa at position 12 is alpha-Methyl-Leu
<220> FEATURE:
<221> NAME/KEY: MOD_RES
<222> LOCATION: (37)..(37)
<223> OTHER INFORMATION: Tyr at position 37 is amidated

<400> SEQUENCE: 8

Lys Cys Glu Thr Ala Thr Cys Ala Thr Gly Xaa Xaa Ala Glu Phe Leu
1               5                   10                  15

Val Arg Ser Ser His Asn Phe Gly Pro Ile Leu Pro Pro Thr Glu Val
            20                  25                  30
```

```
Gly Ser Asn Thr Tyr
        35

<210> SEQ ID NO 9
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is gamma-Glu
<220> FEATURE:
<221> NAME/KEY: MOD_RES
<222> LOCATION: (2)..(7)
<223> OTHER INFORMATION: There is a thioacetal bridge between the
      cysteines at positions 2 and 7
<220> FEATURE:
<221> NAME/KEY: MOD_RES
<222> LOCATION: (26)..(26)
<223> OTHER INFORMATION: The lysine at position 26 is attached to a
      fatty acid linker moiety according to the formula
      (AEEA)2-(gamma-Glu)-CO-(CH2)18-CO2H
<220> FEATURE:
<221> NAME/KEY: MOD_RES
<222> LOCATION: (37)..(37)
<223> OTHER INFORMATION: Tyr at position 37 is amidated

<400> SEQUENCE: 9

Xaa Cys Asn Thr Ala Thr Cys Ala Thr Gly Lys Leu Ala Glu Phe Leu
1               5                   10                  15

Val Arg Ser Ser Asn Asn Phe Gly Pro Lys Leu Pro Pro Thr Glu Val
            20                  25                  30

Gly Ser Asn Thr Tyr
        35

<210> SEQ ID NO 10
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is gamma-Glu
<220> FEATURE:
<221> NAME/KEY: MOD_RES
<222> LOCATION: (2)..(7)
<223> OTHER INFORMATION: There is a thioacetal bridge between the
      cysteines at positions 2 and 7
<220> FEATURE:
<221> NAME/KEY: MOD_RES
<222> LOCATION: (26)..(26)
<223> OTHER INFORMATION: The lysine at position 26 is attached to a
      fatty acid linker moiety according to the formula
      (gamma-Glu)-(AEEA)2-CO-(CH2)18-CO2H
<220> FEATURE:
<221> NAME/KEY: MOD_RES
<222> LOCATION: (37)..(37)
<223> OTHER INFORMATION: Tyr at position 37 is amidated

<400> SEQUENCE: 10

Xaa Cys Asn Thr Ala Thr Cys Ala Thr Gly Lys Leu Ala Glu Phe Leu
1               5                   10                  15

Val Arg Ser Ser Asn Asn Phe Gly Pro Lys Leu Pro Pro Thr Glu Val
            20                  25                  30

Gly Ser Asn Thr Tyr
        35
```

```
<210> SEQ ID NO 11
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is gamma-Glu
<220> FEATURE:
<221> NAME/KEY: MOD_RES
<222> LOCATION: (2)..(7)
<223> OTHER INFORMATION: There is a thioacetal bridge between the
      cysteines at positions 2 and 7
<220> FEATURE:
<221> NAME/KEY: MOD_RES
<222> LOCATION: (26)..(26)
<223> OTHER INFORMATION: The lysine at position 26 is attached to a
      fatty acid linker moiety according to the formula
      (gamma-Glu)2-AEEA-CO-(CH2)18-CO2H
<220> FEATURE:
<221> NAME/KEY: MOD_RES
<222> LOCATION: (37)..(37)
<223> OTHER INFORMATION: Tyr at position 37 is amidated

<400> SEQUENCE: 11

Xaa Cys Asn Thr Ala Thr Cys Ala Thr Gly Lys Leu Ala Glu Phe Leu
1               5                   10                  15

Val Arg Ser Ser Asn Asn Phe Gly Pro Lys Leu Pro Pro Thr Glu Val
            20                  25                  30

Gly Ser Asn Thr Tyr
            35

<210> SEQ ID NO 12
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is gamma-Glu
<220> FEATURE:
<221> NAME/KEY: MOD_RES
<222> LOCATION: (2)..(7)
<223> OTHER INFORMATION: There is a thioacetal bridge between the
      cysteines at positions 2 and 7
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MOD_RES
<222> LOCATION: (26)..(26)
<223> OTHER INFORMATION: The lysine at position 26 is attached to a
      fatty acid linker moiety according to the formula
      (AEEA)2-(gamma-Glu)-CO-(CH2)18-CO2H
<220> FEATURE:
<221> NAME/KEY: MOD_RES
<222> LOCATION: (37)..(37)
<223> OTHER INFORMATION: Tyr at position 37 is amidated

<400> SEQUENCE: 12

Xaa Cys Asn Thr Ala Thr Cys Ala Thr Gln Xaa Leu Ala Glu Phe Leu
1               5                   10                  15

Val Arg Ser Ser Asn Asn Phe Gly Pro Lys Leu Pro Pro Thr Glu Val
            20                  25                  30

Gly Ser Asn Thr Tyr
            35
```

```
<210> SEQ ID NO 13
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is gamma-Glu
<220> FEATURE:
<221> NAME/KEY: MOD_RES
<222> LOCATION: (2)..(7)
<223> OTHER INFORMATION: There is a thioacetal bridge between the
      cysteines at positions 2 and 7
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MOD_RES
<222> LOCATION: (26)..(26)
<223> OTHER INFORMATION: The lysine at position 26 is attached to a
      fatty acid linker moiety according to the formula
      (gamma-Glu)2-CO-(CH2)18-CO2H
<220> FEATURE:
<221> NAME/KEY: MOD_RES
<222> LOCATION: (37)..(37)
<223> OTHER INFORMATION: Tyr at position 37 is amidated

<400> SEQUENCE: 13

Xaa Cys Gly Thr Ala Thr Cys Ala Thr Gly Xaa Leu Ala Glu Phe Leu
 1               5                  10                  15

Val Arg Ser Ser Asn Asn Phe Gly Pro Lys Leu Pro Pro Thr Glu Val
            20                  25                  30

Gly Ser Asn Thr Tyr
            35

<210> SEQ ID NO 14
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is Lys or gamma-Glu
<220> FEATURE:
<221> NAME/KEY: MISC_FEATURE
<222> LOCATION: (3)..(3)
<223> OTHER INFORMATION: Xaa at position 3 is Glu, Asn, or Gly
<220> FEATURE:
<221> NAME/KEY: MISC_FEATURE
<222> LOCATION: (10)..(10)
<223> OTHER INFORMATION: Xaa at position 10 is Gly or Gln
<220> FEATURE:
<221> NAME/KEY: MISC_FEATURE
<222> LOCATION: (11)..(11)
<223> OTHER INFORMATION: Xaa at position 11 is Orn or Lys
<220> FEATURE:
<221> NAME/KEY: MISC_FEATURE
<222> LOCATION: (12)..(12)
<223> OTHER INFORMATION: Xaa at position 12 is Leu or alpha-methyl-Leu
<220> FEATURE:
<221> NAME/KEY: MISC_FEATURE
<222> LOCATION: (15)..(15)
<223> OTHER INFORMATION: Xaa at position 15 is alpha-methyl-Phe or Phe
<220> FEATURE:
<221> NAME/KEY: MISC_FEATURE
<222> LOCATION: (21)..(21)
<223> OTHER INFORMATION: Xaa at position 21 is Asn or His
<220> FEATURE:
```

```
<221> NAME/KEY: MISC_FEATURE
<222> LOCATION: (22)..(22)
<223> OTHER INFORMATION: Xaa at position 22 is N-methyl-Asp, N-methyl-
      Asn, or Asn
<220> FEATURE:
<221> NAME/KEY: MISC_FEATURE
<222> LOCATION: (26)..(26)
<223> OTHER INFORMATION: Xaa at position 26 is Ile or Lys
<220> FEATURE:
<221> NAME/KEY: MOD_RES
<222> LOCATION: (37)..(37)
<223> OTHER INFORMATION: C-terminus is amidated

<400> SEQUENCE: 14

Xaa Cys Xaa Thr Ala Thr Cys Ala Thr Xaa Xaa Xaa Ala Glu Xaa Leu
1               5                   10                  15

Val Arg Ser Ser Xaa Xaa Phe Gly Pro Xaa Leu Pro Pro Thr Glu Val
            20                  25                  30

Gly Ser Asn Thr Tyr
            35

<210> SEQ ID NO 15
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (2)..(7)
<220> FEATURE:
<221> NAME/KEY: MOD_RES
<222> LOCATION: (37)..(37)
<223> OTHER INFORMATION: Tyr at position 37 is amidated

<400> SEQUENCE: 15

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
            35

<210> SEQ ID NO 16
<211> LENGTH: 32
<212> TYPE: PRT
<213> ORGANISM: Homo sapiens
<220> FEATURE:
<221> NAME/KEY: DISULFID
<222> LOCATION: (1)..(7)
<220> FEATURE:
<221> NAME/KEY: MOD_RES
<222> LOCATION: (32)..(32)
<223> OTHER INFORMATION: Pro at position 32 is amidated

<400> SEQUENCE: 16

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 17
<211> LENGTH: 37
<212> TYPE: PRT
<213> ORGANISM: Homo sapiens
<220> FEATURE:
<221> NAME/KEY: DISULFID
<222> LOCATION: (2)..(7)
```

```
<220> FEATURE:
<221> NAME/KEY: MOD_RES
<222> LOCATION: (37)..(37)
<223> OTHER INFORMATION: Tyr at position 37 is amidated

<400> SEQUENCE: 17

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 18
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (20)..(20)
<223> OTHER INFORMATION: The lysine at position 20 is attached to a
      fatty acid linker moiety according to the formula
      (2-[2-(2-Amino-ethoxy)-ethoxy]-acetyl)2-
      (gamma-Glu)-CO-(CH2)16-CO2H

<400> SEQUENCE: 18

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 19
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (20)..(20)
<223> OTHER INFORMATION: Lys at position 20 is chemically modified by
      conjugation of the epsilon-amino group of the Lys side chain with
      (2-[2-(2-amino-ethoxy)-ethoxy]-acetyl)2-
      (gamma-Glu)-CO-(CH2)18-CO2H
<220> FEATURE:
<221> NAME/KEY: MOD_RES
<222> LOCATION: (34)..(34)
<223> OTHER INFORMATION: Gly at position 34 is amidated

<400> SEQUENCE: 19

His Xaa Gln Gly Thr Phe Thr Ser Asp Tyr Ser Lys Tyr Leu Asp Glu
1               5                   10                  15

Lys Lys Ala Lys Glu Phe Val Glu Trp Leu Leu Glu Gly Gly Pro Ser
            20                  25                  30

Ser Gly

<210> SEQ ID NO 20
<211> LENGTH: 39
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-Methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(gamma-Glu)-CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 20

Tyr Xaa Gln Gly Thr Phe Thr Ser Asp Tyr Ser Ile Xaa Leu Asp Lys
1               5                   10                  15

Lys Ala Gln Xaa Ala Phe Ile Glu Tyr Leu Leu Glu Gly Gly Pro Ser
            20                  25                  30

Ser Gly Ala Pro Pro Pro Ser
        35

<210> SEQ ID NO 21
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is Aib
<220> FEATURE:
<221> NAME/KEY: MOD_RES
<222> LOCATION: (20)..(20)
<223> OTHER INFORMATION: K at position 20 is chemically modified through
      conjugation to the epsilon-amino group of the K side-chain with
      (2-[2-(2-Amino-ethoxy)-ethoxy]-acetyl)2-
      (gamma-Glu)1-CO-(CH2)18-CO2H
<220> FEATURE:
<221> NAME/KEY: MOD_RES
<222> LOCATION: (39)..(39)
<223> OTHER INFORMATION: Serine is amidated as a C-terminal primary
      amide

<400> SEQUENCE: 21

Tyr Xaa Glu Gly Thr Phe Thr Ser Asp Tyr Ser Ile Xaa Leu Asp Lys
1               5                   10                  15

Ile Ala Gln Lys Ala Phe Val Gln Trp Leu Ile Ala Gly Gly Pro Ser
            20                  25                  30

Ser Gly Ala Pro Pro Pro Ser
        35

<210> SEQ ID NO 22
```

```
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is gamma-Glu
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MISC_FEATURE
<222> LOCATION: (15)..(15)
<223> OTHER INFORMATION: Xaa at position 15 is alpha-Me-Phe
<220> FEATURE:
<221> NAME/KEY: MISC_FEATURE
<222> LOCATION: (22)..(22)
<223> OTHER INFORMATION: Xaa at position 22 is N-Me-Asn
<220> FEATURE:
<221> NAME/KEY: MOD_RES
<222> LOCATION: (37)..(37)
<223> OTHER INFORMATION: Tys at position 37 is amidated

<400> SEQUENCE: 22

Xaa Cys Asn Thr Ala Thr Cys Ala Thr Gly Xaa Leu Ala Glu Xaa Leu
1               5                   10                  15

Val Arg Ser Ser Asn Xaa Phe Gly Pro Lys Leu Pro Pro Thr Glu Val
            20                  25                  30

Gly Ser Asn Thr Tyr
            35

<210> SEQ ID NO 23
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is gamma-Glu
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MISC_FEATURE
<222> LOCATION: (15)..(15)
<223> OTHER INFORMATION: Xaa at position 15 is alpha-Me-Phe
<220> FEATURE:
<221> NAME/KEY: MISC_FEATURE
<222> LOCATION: (22)..(22)
<223> OTHER INFORMATION: Xaa at position 22 is N-Me-Asp
<220> FEATURE:
<221> NAME/KEY: MOD_RES
<222> LOCATION: (37)..(37)
<223> OTHER INFORMATION: Tys at position 37 is amidated

<400> SEQUENCE: 23

Xaa Cys Asn Thr Ala Thr Cys Ala Thr Gly Xaa Leu Ala Glu Xaa Leu
1               5                   10                  15

Val Arg Ser Ser Asn Xaa Phe Gly Pro Lys Leu Pro Pro Thr Glu Val
            20                  25                  30

Gly Ser Asn Thr Tyr
            35

<210> SEQ ID NO 24
<211> LENGTH: 37
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MISC_FEATURE
<222> LOCATION: (15)..(15)
<223> OTHER INFORMATION: Xaa at position 15 is alpha-Me-Phe
<220> FEATURE:
<221> NAME/KEY: MISC_FEATURE
<222> LOCATION: (22)..(22)
<223> OTHER INFORMATION: Xaa at position 22 is N-Me-Asp
<220> FEATURE:
<221> NAME/KEY: MOD_RES
<222> LOCATION: (37)..(37)
<223> OTHER INFORMATION: Tys at position 37 is amidated

<400> SEQUENCE: 24

Lys Cys Glu Thr Ala Thr Cys Ala Thr Gly Xaa Leu Ala Glu Xaa Leu
1               5                   10                  15

Val Arg Ser Ser Asn Xaa Phe Gly Pro Ile Leu Pro Pro Thr Glu Val
            20                  25                  30

Gly Ser Asn Thr Tyr
            35

<210> SEQ ID NO 25
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa at position 11 is Orn
<220> FEATURE:
<221> NAME/KEY: MISC_FEATURE
<222> LOCATION: (12)..(12)
<223> OTHER INFORMATION: Xaa at position 12 is alpha-Me-Leu
<220> FEATURE:
<221> NAME/KEY: MOD_RES
<222> LOCATION: (37)..(37)
<223> OTHER INFORMATION: Tys at position 37 is amidated

<400> SEQUENCE: 25

Lys Cys Glu Thr Ala Thr Cys Ala Thr Gly Xaa Xaa Ala Glu Phe Leu
1               5                   10                  15

Val Arg Ser Ser His Asn Phe Gly Pro Ile Leu Pro Pro Thr Glu Val
            20                  25                  30

Gly Ser Asn Thr Tyr
            35
```

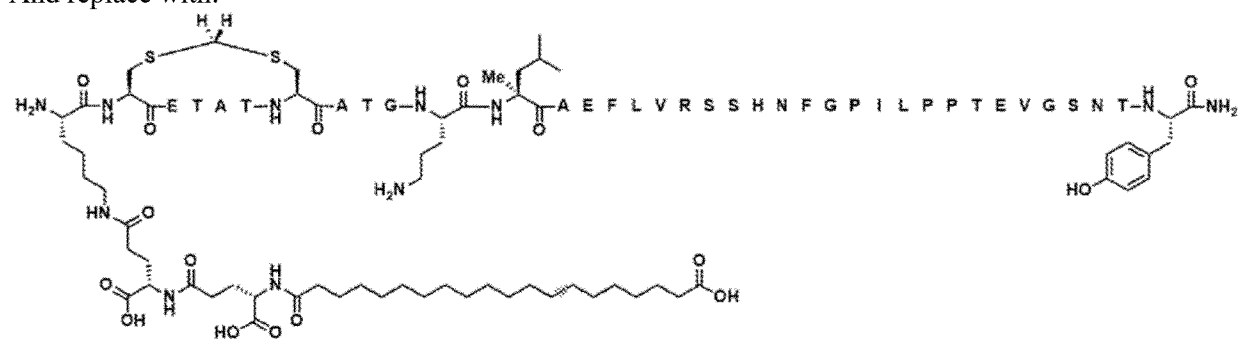

The invention claimed is:

1. A compound comprising SEQ ID NO:2 or a pharmaceutically acceptable salt thereof.

2. A compound comprising SEQ ID NO:4 or a pharmaceutically acceptable salt thereof.

3. A compound comprising SEQ ID NO:6 or a pharmaceutically acceptable salt thereof.

4. A compound comprising SEQ ID NO:8 or a pharmaceutically acceptable salt thereof.

5. A compound consisting of SEQ ID NO:2 or a pharmaceutically acceptable salt thereof.

6. A compound consisting of SEQ ID NO:4 or a pharmaceutically acceptable salt thereof.

7. A compound consisting of SEQ ID NO:6 or a pharmaceutically acceptable salt thereof.

8. A compound consisting of SEQ ID NO:8 or a pharmaceutically acceptable salt thereof.

9. A method of treating Type 2 diabetes in a patient in need thereof, comprising administering to the patient an effective amount of a compound according to any one of claims 5-8 or 1-4, or a pharmaceutically acceptable salt thereof.

10. A method of treating obesity in a patient in need thereof, comprising administering to the patient an effective amount of a compound according to any one of claims 5-8 or 1-4, or a pharmaceutically acceptable salt thereof.

11. A method of treating dyslipidemia in a patient in need thereof, comprising administering to the patient an effective amount of a compound according to any one of claims 5-8 or 1-4, or a pharmaceutically acceptable salt thereof.

12. A method of treating NASH in a patient in need thereof, comprising administering to the patient an effective amount of a compound according to any one of claims 5-8 or 1-4, or a pharmaceutically acceptable salt thereof.

13. A method of lowering food intake by inducing satiety in a patient in need thereof, comprising administering to the patient an effective amount of a compound according to any one of claims 5-8 and 1-4, or a pharmaceutically acceptable salt thereof.

14. A method of lowering body weight by lowering food intake by inducing satiety in a patient in need thereof, comprising administering to the patient an effective amount of a compound according to any one of claims 5-8 or 1-4, or a pharmaceutically acceptable salt thereof.

15. A method of lowering blood glucose in a patient in need thereof, comprising administering to the patient an effective amount of a compound according to any one of claims 5-8 or 1-4, or a pharmaceutically acceptable salt thereof.

16. A method of lowering triglycerides in a patient in need thereof, comprising administering to the patient an effective amount of a compound according to any one of claim 5-8 or 1-4, or a pharmaceutically acceptable salt thereof.

17. A pharmaceutical composition comprising a compound according to any one of claims 5-8 or 1-4, or a pharmaceutically acceptable salt thereof, in combination with one or more pharmaceutically acceptable carriers, diluents, or excipients.

18. A method of treating a condition in a patient in need thereof, comprising administering to the patient an effective amount of the compound of any one of claims 5-8 or 1-4 and an effective amount of an additional agent, wherein the condition is selected from the group consisting of clinical or pre-clinical diabetes, obesity, NASH, and dyslipidemia.

19. The method of treatment according to claim 18 wherein the additional agent is an incretin or incretin analog.

20. The method of treatment according to claim 19 wherein the incretin or incretin analog is SEQ ID NO:21.

* * * * *

UNITED STATES PATENT AND TRADEMARK OFFICE
CERTIFICATE OF CORRECTION

PATENT NO. : 12,115,210 B2
APPLICATION NO. : 17/684578
DATED : October 15, 2024
INVENTOR(S) : Milata Mary Abraham et al.

It is certified that error appears in the above-identified patent and that said Letters Patent is hereby corrected as shown below:

In the Specification

1) At Column 31, Line 50, delete:

"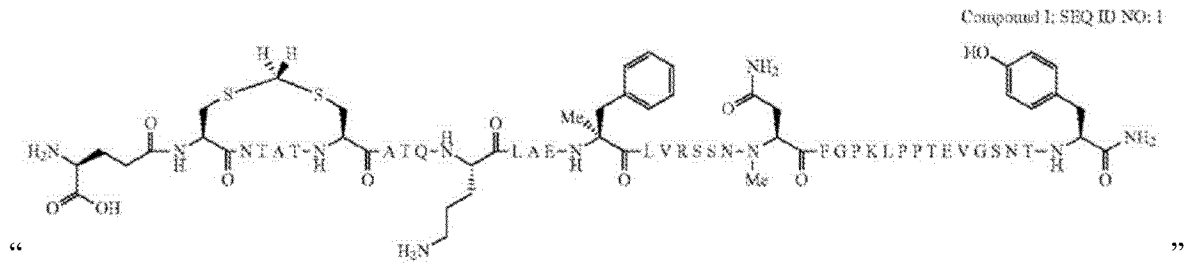"

And replace with:

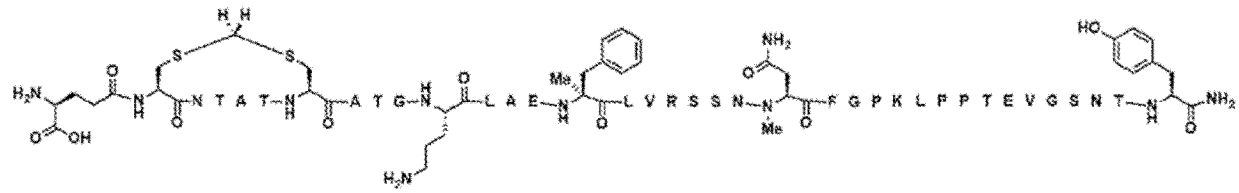

Signed and Sealed this
Twenty-ninth Day of April, 2025

Coke Morgan Stewart
*Acting Director of the United States Patent and Trademark Office*

CERTIFICATE OF CORRECTION (continued)
U.S. Pat. No. 12,115,210 B2

2) At Column 33, Line 1, delete:

"
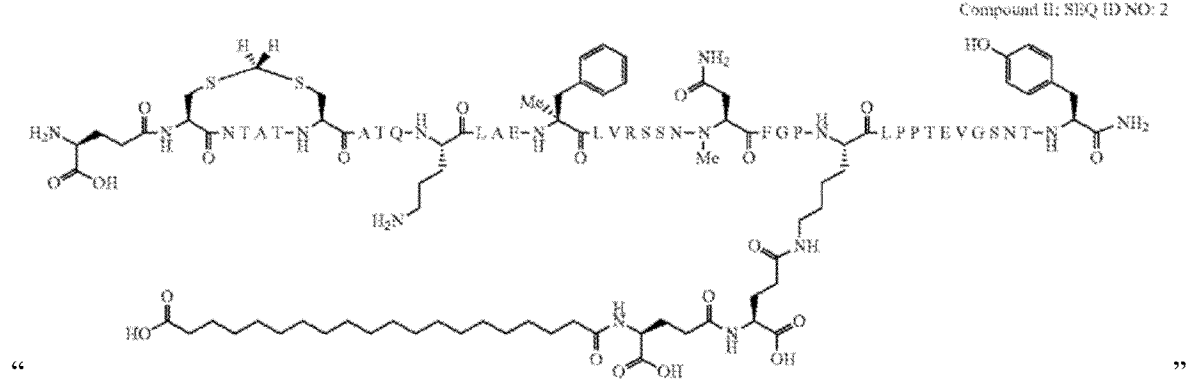
"

And replace with:

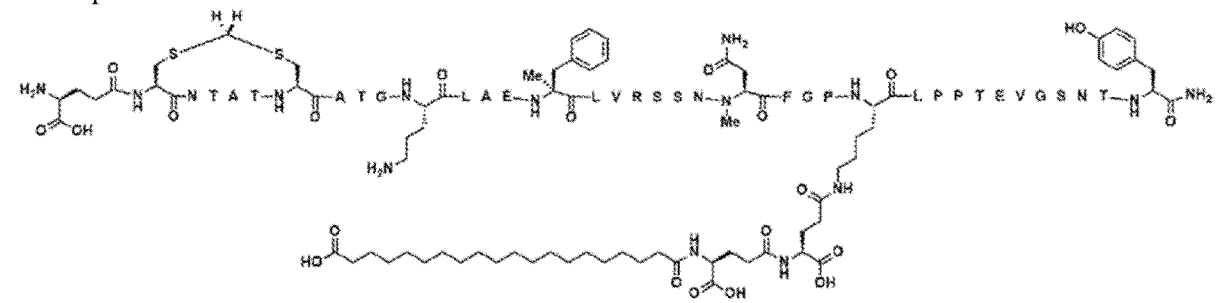

3) At Column 33, Line 40, delete:

"
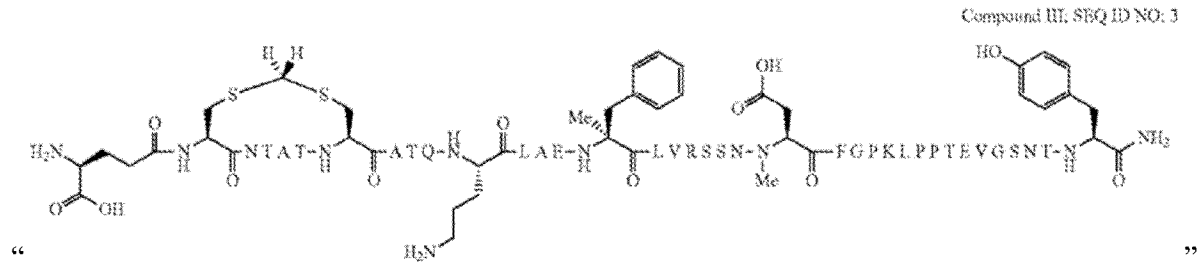
"

And replace with:

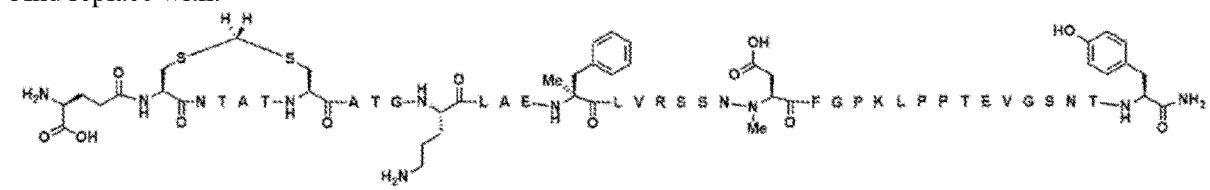

4) At Column 35, Line 1, delete:
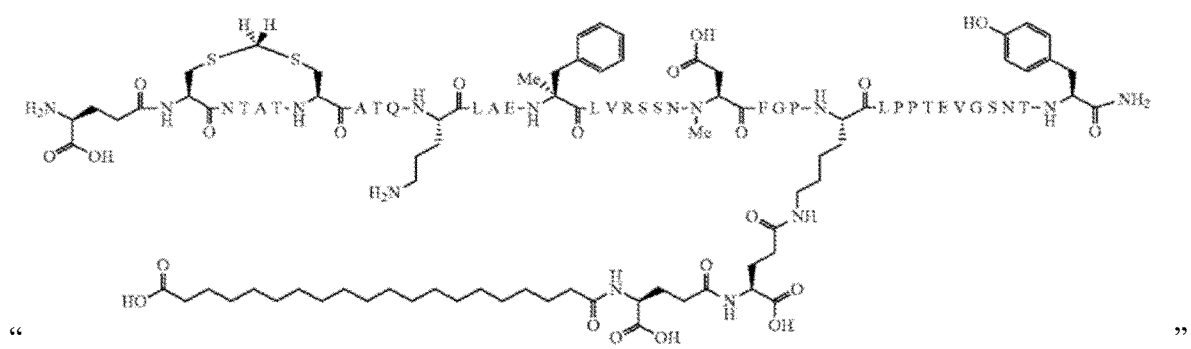
"                                                                                              "
And replace with:
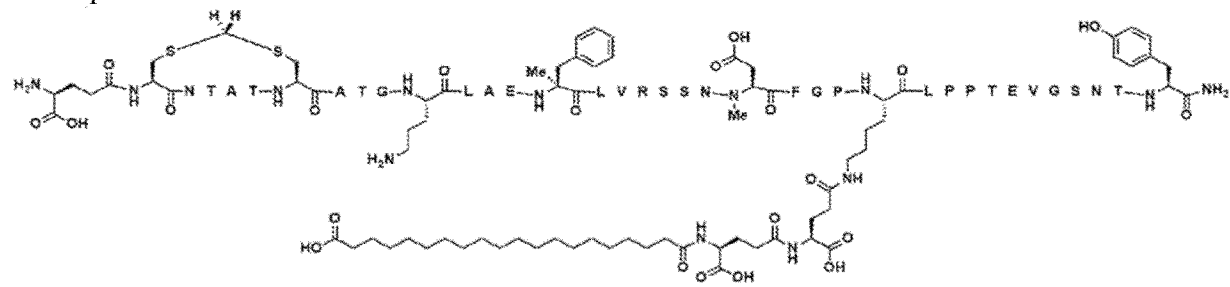
5) At Column 35, Line 37, delete:
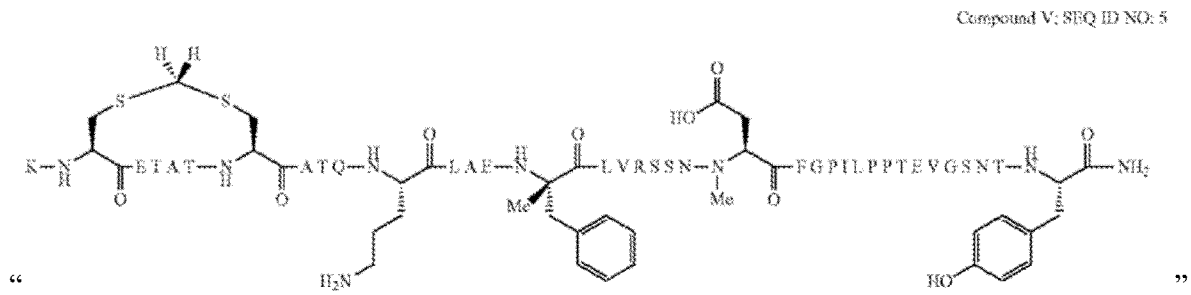
"                                                                                              "
And replace with:
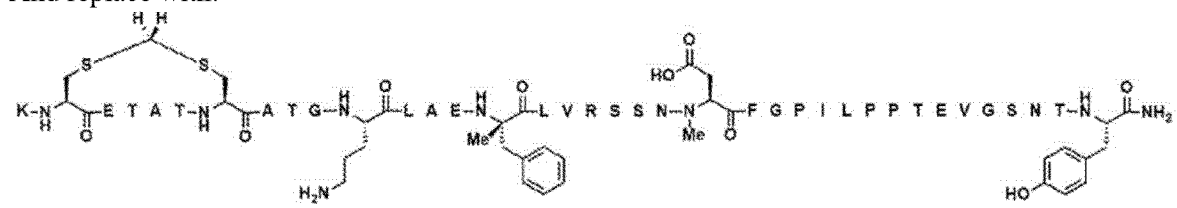

CERTIFICATE OF CORRECTION (continued)
U.S. Pat. No. 12,115,210 B2

Page 4 of 5

6) At Column 37, Line 1, delete:

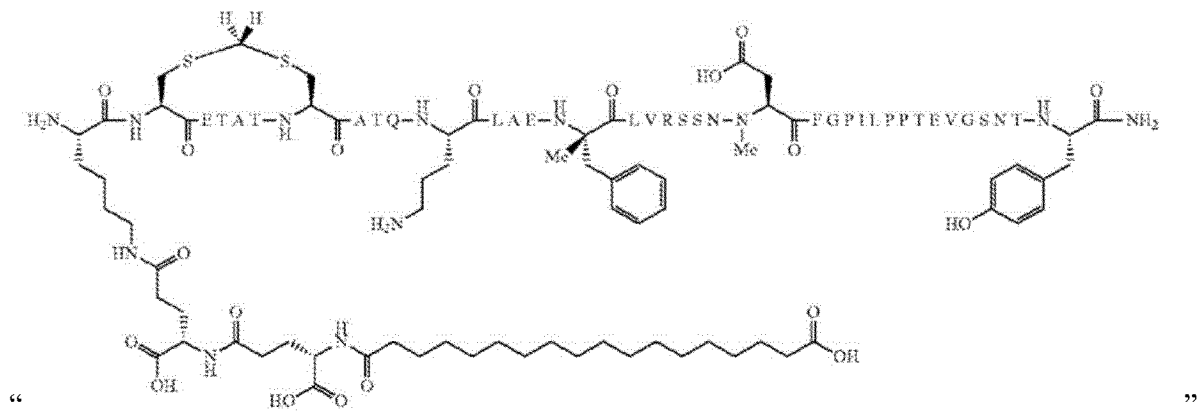

" "

And replace with:

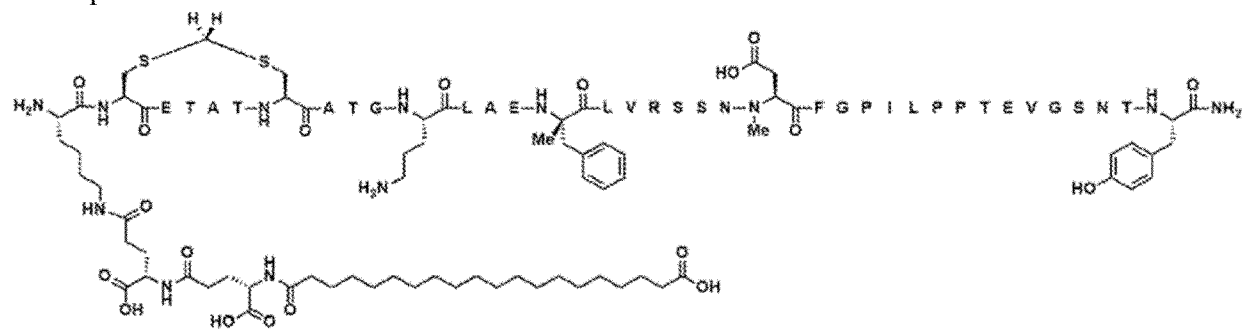

7) At Column 37, Line 37, delete:

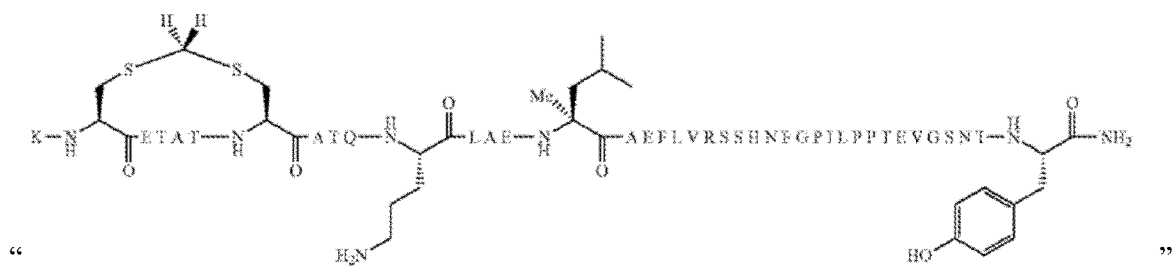

" "

And replace with:

CERTIFICATE OF CORRECTION (continued)
U.S. Pat. No. 12,115,210 B2

8) At Column 39, Line 1, delete:

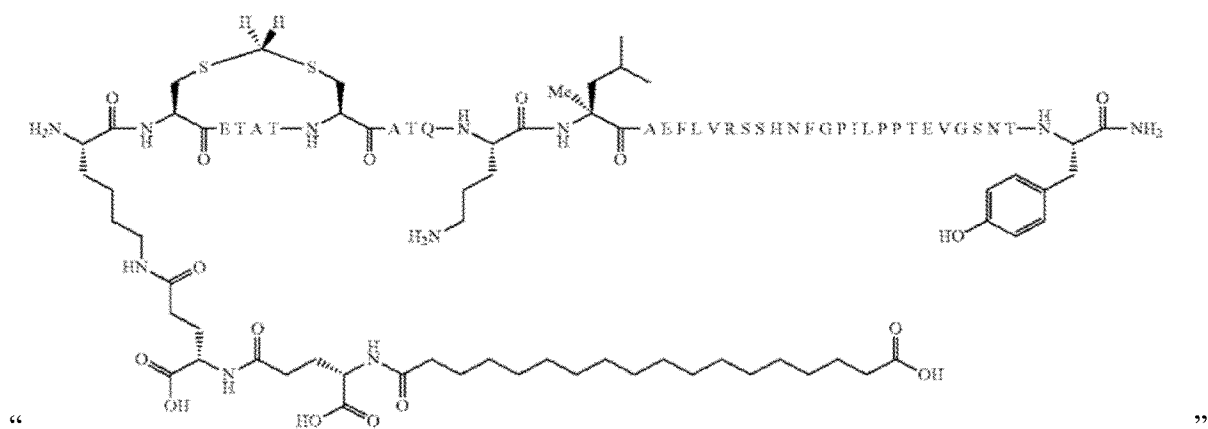

"

"

And replace with: